US006844178B2

(12) United States Patent
Bolen et al.

(10) Patent No.: US 6,844,178 B2
(45) Date of Patent: Jan. 18, 2005

(54) RECOMBINANT KID PREGASTRIC ESTERASE AND METHODS FOR ITS PRODUCTION AND USE

(75) Inventors: Paul L. Bolen, Middletown, NJ (US); Paul L. Cihak, Leonardo, NJ (US); Lewis G. Scharpf, Jr., Fair Haven, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 77 days.

(21) Appl. No.: 10/420,564

(22) Filed: Apr. 22, 2003

(65) Prior Publication Data

US 2004/0001819 A1 Jan. 1, 2004

Related U.S. Application Data

(62) Division of application No. 10/043,665, filed on Jan. 14, 2002, now Pat. No. 6,582,948, which is a division of application No. 09/186,489, filed on Nov. 5, 1998, now Pat. No. 6,375,947.

(51) Int. Cl.$^7$ .............................. C12N 9/16; C12N 1/20; C12N 15/00; C07H 21/04
(52) U.S. Cl. ........................ 435/198; 435/196; 435/197; 435/252.3; 435/320.1; 554/1; 536/23.2
(58) Field of Search ................................. 435/198, 197, 435/196, 252.3, 320.1; 536/23.2; 554/1

(56) References Cited

U.S. PATENT DOCUMENTS

| 2,531,329 A | 11/1950 | Farnham ...................... 426/35 |
| 2,794,743 A | 4/1957 | Farnham ...................... 426/63 |
| 3,081,225 A | 3/1963 | Farnham et al. ............. 424/94.6 |
| 3,256,150 A | 6/1966 | Nelson et al. ............... 424/94.6 |
| 5,320,959 A | 6/1994 | Peters et al. ................ 435/198 |
| 5,372,941 A | 12/1994 | Peters et al. ................ 435/198 |
| 5,521,088 A | 5/1996 | Fujii et al. ................ 435/254.2 |
| 5,529,917 A | 6/1996 | Andreoli et al. ............ 435/198 |
| 5,691,181 A | 11/1997 | Lowe ......................... 435/325 |

FOREIGN PATENT DOCUMENTS

| EP | 0 502 474 | 9/1992 |
| FR | 542629 | 5/1993 |
| FR | WO94/13816 | 6/1994 |
| GB | WO86/01532 | 3/1986 |
| WO | WO 86/03778 | 7/1986 |

OTHER PUBLICATIONS

Titus, et al, Crystal Structure of Human Homogentisate Dioxygenase, Nature Structural Biology, Jul. 2000, vol. 7, No. 7, pp. 542–546.
Brockerhoff, H., "Determination of the Positional Distribution of Fatty Acids in Glycerolipids", General Analytical Methods, 315–325.
Chapter, 12, "Hard Italian Cheeses", Cheese and Fermented Milk Foods, 213–227.

Eastman Kodak Company, "Yeast N–Terminal FLAG® Expression System", FLAG Biosystem 1994.
Food Chemicals Codex, National Academy Press, (Washington, D.C. 1981), pp. 480–493.
Parry, R.M., Jr., et al, "Rapid and Sensitive Assay for Milk Lipase", Journal of Dairy Science 49, 356–360.
Invitrogen Corp., "Pichia Expression Kit:Protein Expression" Version 3.0, Calalog No. K1710–01.
Ramsey, Harold A., "Electrophoretic Separation of Esterases Present in Various Tissues of the Calf", Journal of Dairy Science, 1185–1186.
Ramsey, Harold A., "Photometric Procedure for Determining Esterase Activity", Clinical Chemistry 3:185–194.
Ramsey Harold A and Young, J.W., "Substrate Specificity of Pregastric Esterase from the Calf", Journal of Dairy Science, 2304–2306.
Sambrook, J., et al, "Molecular Cloning:A Laboratory Manual", (Cold Spring Harbor, 1989).
Scorer, Carol A., et al, "Rapid Selection Using G418 of High Copy Number Transformants of Pichia pastoris for high–level Foreign Gene Expression", Bio/Technology 12:181 (Feb. 12, 1994.
Anderson, R.A. and Sando, G.N.J. Biol.Chem. 26:22740–84 (1991).
Bernbach, et al., Eur.J.Biochem. 148:233–238 (1985).
Birschbach, Bulletin of the IDF 269:36–39 (1992).
Carriere, F., et al, Eur.J.Biochem. 202:75–83 (1991).
Godfrey and West Eds. Chapter 2.12 Industrial Enzymology, $2^{nd}$ Ed. Stockton Press, 1996.
Chaudhari & Richardson, J. of Dairy Science 54:467–71 (1971).
Crabbe, et al, Protein Expression and Purification, 7:229–236 (1996).
DeLaborde de Monpesat, et al, Chemical Abstracts 114:278 (1991).
Docherty, et al, Nuc. Ac. Res. 13:1891–1903 (1985).
D'Souza & Oriel, Appl. Biochem. And Biotech. 36:183–198 (1992).
Fox & Law, Food Biotechnology 5:239–262 (1991).
Ha & Lindsay, Chem. Abstr. 118:85–66 (1993).
Ha & Lindsay, Int. Dairy Journ. 2:179–193 (1992).

(List continued on next page.)

Primary Examiner—Tekchand Saidha
(74) Attorney, Agent, or Firm—Joseph F. Leightner

(57) ABSTRACT

The present invention provides kPGE and derivative polypeptides which are capable of being produced by genetic recombination and used to produce EMCs. This invention further provides nucleic acid sequences encoding kPGE and derivative polypeptides which can be used to create recombinant host cells that express kPGE and derivative polypeptides. A further subject of the present of invention is a fusion polypeptide called polyHis-enterokinase which increases expression of esterases and lipases when fused to the N-terminal of the esterase or lipase. This invention also provides a method for treating animals with an esterase or lipase deficiency by administering rkPGE to the animal in a therapeutically effective amount.

3 Claims, 15 Drawing Sheets

OTHER PUBLICATIONS

Hamosh, N., Nutrition 6:421–428 (1990).
Lai, et al, JAOCS 75:411–416 (1998).
Komaromy & Schotz, PNAS USA 84:626–630 (1987).
Moreau, et al, Biochem. And Biophys. Acta 960:286–293 (1988).
Nelson, et al., J.Dairy Sci. 60:327–362 (1976).
Richardson, et al., J.Dairy Sci. 54:643–647 (1970).
Richardson & Nelson, J.Dairy Sci 50:1061–1065 (1967).
Siezen & van den Berg, Bulletin of the IDF 294:4–6 (1994).
Sweet et al., Arch.Biochem. and Biophys., 234:144–150 (1984).
Timmermans, et al., Gene 147:259–262 (1994).
Vonderwulbecke, et al., Enzyme Microb. Technol. 14:631–39 (1992).

Comparison of Amino Acid Sequences of
Kid Pregastric Esterase (K-PGE)
Bovine Pregastric Esterase (B-PGE)
Human Gastric Lipase (HGL)
Rat Lingual Lipase (RLL)

```
              10         20         30         40         50         60
              *    *     *    *     *    *     *    *     *    *     *    *
K-PGE   FLGKIAKNPE ASMNVSQMIS FWGYPSEMHK VITADGYILQ VYRIPHGKND ANHLGQRPVV
B-PGE   FLGKIAKNPE ASMNVSQMIS YWGYPSEMHK VITADGYILQ VYRIPHGKNN ANHLGQRPVV
HGL     LFGKLHPGSPE VTMNISQMIT YWGYPNEEYE VVTEDGYILE VNRIPYGKKN SGNTGQRPVV
RLL     LFGKLGPGNPE ANMNISQMIT YWGYPCQEYE VVTEDGYILG VYRIPHGKNN SENIGKRPVV 70         80         90        100        110        120
              *    *     *    *     *    *     *    *     *    *     *    *
K-PGE   FLQHGLLASA TNWISNLPNN SLGFLLADAG YDVWLGNSRG NIWAQEHLYY SPDSPEFWAF
B-PGE   FLQHGLLGSA TNWISNLPKN SLGFLLADAG YDVWLGNSRG NIWAQEHLYY SPDSPEFWAF
HGL     FLQHGLLASA TNWISNLPNN SLAFILADAG YDVWLGNSRG NTWARRNLYY SPDSVEFWAF
RLL     YLQHGLIASA TNWIANLPNN SLAFMLADAG YDVWLGNSRG NTWSRKNVYY SPDSVEFWAF 130        140        150        160        170        180
              *    *     *    *     *    *     *    *     *    *     *    *
K-PGE   SFDEMAEYDL PSTIDFILKR TGQKKLHYVG HSQGTTIGFV AFSTNPTLAE KIEVFHALAP
B-PGE   SFDEMAEYDL PSTIDFILRR TGQKKLHYVG HSQGTTIGFI AFSTSPTLAE KIKVFYALAP
HGL     SFDEMAKYDL PATIDFIVKK TGQKQLHYVG HSQGTTIGFI AFSTNPSLAK RIKTFYALAP
RLL     SFDEMAKYDL PATINFIVQK TGQEKIHYVG HSQGTTIGFI AFSTNPTLAK KIKTFYALAP 190        200        210        220        230        240
              *    *     *    *     *    *     *    *     *    *     *    *
K-PGE   VATVKHTQSL FNKLALIPHF LFKIIFGNKM FYPHNFFEQF LGVEVCSRET LDVLCKNALF
B-PGE   VATVKYTKSL FNKLALIPHF LFKIIFGDKM FYPHTFLEQF LGVEMCSRET LDVLCKNALF
HGL     VATVKYTKSL INKLRFVPQS LFKFIFGDKI FYPHNFFDQF LATEVCSREM LNLLCSNALF
RLL     VATVKYTQSP LKKISFIPTF LFKLMFGKKM FLPHTYFDDF LGTEVCSREV LDLLCSNTLF 250        260        270        280        290        300
              *    *     *    *     *    *     *    *     *    *     *    *
K-PGE   AITGADNKNF NMSRLDVYVA HNPAGASVQN ILHWRQAIKS GKFQAFDWGA SVENLMHYNQ
B-PGE   AITGVDNKNF NMSRLDVYIA HNPAGTSVQN TLHWRQAVKS GKFQAFDWGA PYQNLMHYHQ
HGL     IICGFDSKNF NTSRLDVYLS HNPAGTSVQN MFHWTQAVKS GKFQAYDWGS PVQNRMHYDQ
RLL     IFCGFDKKNL NVSRFDVYLG HNPAGTSVQD FLHWAQLVRS GKFQAFNWGS PSQNMLHYNQ 310        320        330        340        350        360
              *    *     *    *     *    *     *    *     *    *     *    *
K-PGE   PTPPIYNLTA MNVPIAVWSA GQDLLADPQD VDLLLSKLSN LIHHKEIPNY NHLDFIWAMD
B-PGE   PTPPIYNLTA MNVPIAVWSA DNDLLADPQD VDFLLSKLSN LIYHKEIPNY NHLDFIWAMD
HGL     SQPPYYNVTA MNVPIAVWNG GKDLLADPQD VGLLLPKLPN LIYHKEIPFY NHLDFIWAMD
RLL     KTPPEYDVSA MTVPVAVWNG GNDILADPQD VAMLLPKLSN LLFHKEILAY NHLDFIWAMD

370
              *    *     *
K-PGE   APQEVYNEII SLMAKDKK
B-PGE   APQEVYNEIV SLMAEDKK
HGL     APQEVYNDIV SMISEDKK
RLL     APQEVYNEMI SMMAED
```

FIG. 1

Comparison of Kid and Bovine Pregastric Esterase Genes

```
                       10         20         30         40         50         60
                    *    *     *    *     *    *     *    *     *    *     *    *
BOVINE PGE   TTCCTTGGAA AAATTGCTAA GAACCCTGAA GCCAGTATGA ATGTtAGTCA GATGATTTCC>

KID PGE      TTCCTTGGAA AAATTGCTAA GAACCCTGAA GCCAGTATGA ATGTGAGTCA GATGATTTCC 70         80         90        100        110        120
                    *    *     *    *     *    *     *    *     *    *     *    *
BOVINE PGE   TaCTGGGGCT ACCCAAGTGA GATGCATAAA GTTATAACTG CgGATGGtTA TATCCTTCAG>

KID PGE      TTCTGGGGCT ACCCAAGTGA GATGCATAAA GTTATAACTG CAGATGGCTA TATCCTTCAG 130        140        150        160        170        180
                    *    *     *    *     *    *     *    *     *    *     *    *
BOVINE PGE   GTCTATCGGA TTCCTCATGG AAAGAATaAT GCTAATCATT TAGGTCAGAG ACCTGTTGTG>

KID PGE      GTCTATCGGA TTCCTCATGG AAAGAATGAT GCTAATCATT TAGGTCAGAG ACCTGTTGTG 190        200        210        220        230        240
                    *    *     *    *     *    *     *    *     *    *     *    *
BOVINE PGE   TTTCTGCAGC ATGGTCTTCT TGgaTCAGCc ACAAACTGGA TTTCCAACCT gCCCAAgAAC>

KID PGE      TTTCTGCAGC ATGGTCTTCT TGCCTCAGCT ACAAACTGGA TTTCCAACCT TCCCAACAAC 250        260        270        280        290        300
                    *    *     *    *     *    *     *    *     *    *     *    *
BOVINE PGE   AGCCTGGGCT TCCTCCTGGC AGATGCTGGT TATGACGTGT GGCTGGGGAA CAGCAGAGGA>

KID PGE      AGCCTGGGCT TCCTCCTGGC AGATGCTGGT TATGACGTGT GGCTGGGGAA CAGCAGAGGA 310        320        330        340        350        360
                    *    *     *    *     *    *     *    *     *    *     *    *
BOVINE PGE   AACACcTGGG CCCAGGAACA TTTATACTAT TCACCAGACT CCCCgGAATT CTGGGCTTTC>

KID PGE      AACACTTGGG CCCAGGAACA TTTATACTAT TCACCAGACT CCCCTGAATT CTGGGCTTTC 370        380        390        400        410        420
                    *    *     *    *     *    *     *    *     *    *     *    *
BOVINE PGE   AGCTTTGATG AAATGGCgGA ATATGACCTT CCATCTACAA TTGATTTCAT CTTAAgGAGA>

KID PGE      AGCTTTGATG AAATGGCTGA ATATGACCTT CCATCTACAA TTGATTTCAT CTTAAAGAGA 430        440        450        460        470        480
                    *    *     *    *     *    *     *    *     *    *     *    *
BOVINE PGE   ACAGGACAGA AGAAGCTACA CTATGTTGGC CATTCCCAAG GCACCACCAT TGGTTTTaTC>

KID PGE      ACAGGACAGA AGAAGCTACA CTATGTTGGC CATTCCCAAG GCACCACCAT TGGTTTTGTC
```

FIG. 2(A)

```
                      490         500         510         520         530         540
                       *     *     *     *     *     *     *     *     *     *     *     *
BOVINE PGE    GCCTTTTCTA CCAgTCCCAC AtTGGCTGAA AAAATCaAAG TCTTCtATGC ATTAGCCCCA>
              ^^^^^^^^^^ ^^^_^^^^^^ ^_^^^^^^^^ ^^^^^^_^^^ ^^^^^_^^^^ ^^^^^^^^^^
KID PGE       GCCTTTTCTA CCAATCCCAC ACTGGCTGAA AAAATCGAAG TCTTCCATGC ATTAGCCCCA 550         560         570         580         590         600
                       *     *     *     *     *     *     *     *     *     *     *     *
BOVINE PGE    GTtGCCACAG TGAAGtACAC CaAGAGCCTG TTTAACAAAC TTGCACTTAT TCCTCACTTC>
              ^^_^^^^^^^ ^^^^^_^^^^ ^_^^^^^^^^ ^^^^^^^^^^ ^^^^^^^^^^ ^^^^^^^^^^
KID PGE       GTCGCCACAG TGAAGCACAC CCAGAGCCTG TTTAACAAAC TTGCACTTAT TCCTCACTTC 610         620         630         640         650         660
                       *     *     *     *     *     *     *     *     *     *     *     *
BOVINE PGE    CTCTTCAAGA TTATATTTGG TgACAAAATG TTCTACCCAC ACAcTTTTTT gGAACAATTT>
              ^^^^^^^^^^ ^^^^^^^^^^ ^_^^^^^^^^ ^^^^^^^^^^ ^^^_^^^^^^ _^^^^^^^^^
KID PGE       CTCTTCAAGA TTATATTTGG TAACAAAATG TTCTACCCAC ACAATTTTTT TGAACAATTT 670         680         690         700         710         720
                       *     *     *     *     *     *     *     *     *     *     *     *
BOVINE PGE    CTTGGTGTTG AAaTGTGCTC cCGTGAGACA CTGGATGTCC TTTGTAAGAA TGCCTTGTTT>
              ^^^^^^^^^^ ^^_^^^^^^^ _^^^^^^^^^ ^^^^^^^^^^ ^^^^^^^^^^ ^^^^^^^^^^
KID PGE       CTTGGTGTTG.AAGTGTGCTC .TCGTGAGACA CTGGATGTCC TTTGTAAGAA TGCCTTGTTT 730         740         750         760         770         780
                       *     *     *     *     *     *     *     *     *     *     *     *
BOVINE PGE    GCCATTACTG GAGttGACAA TAAAAACTTC AACATGAGTC GCTTAGATGT GTATaTAGCA>
              ^^^^^^^^^^ ^^^_^^^^^^ ^^^^^^^^^^ ^^^^^^^^^^ ^^^^^^^^^^ ^^^^_^^^^^
KID PGE       GCCATTACTG GAGCTGACAA TAAAAACTTC AACATGAGTC GCTTAGATGT GTATGTAGCA 790         800         810         820         830         840
                       *     *     *     *     *     *     *     *     *     *     *     *
BOVINE PGE    CATAATCCAG CAGGAaCTTC TGTTCAAAAC AcCCTCCACT GGAGACAGGC TgTTAAGTCT>
              ^^^^^^^^^^ ^^^^^_^^^^ ^^^^^^^^^^ ^_^^^^^^^^ ^^^^^^^^^^ ^_^^^^^^^^
KID PGE       CATAATCCAG CAGGAGCTTC TGTTCAAAAC ATCCTCCACT GGAGACAGGC TATTAAGTCT 850         860         870         880         890         900
                       *     *     *     *     *     *     *     *     *     *     *     *
BOVINE PGE    GGGAAATTCC AAGCTTTTGA CTGGGGAGCC cCAtaTcAGA ACCTAATGCA TTATcATCAG>
              ^^^^^^^^^^ ^^^^^^^^^^ ^^^^^^^^^^ _^^___^_^^^ ^^^^^^^^^^ ^^^^_^^^^^
KID PGE       GGGAAATTCC AAGCTTTTGA CTGGGGAGCC TCAGTTGAGA ACCTAATGCA TTATAATCAG 910         920         930         940         950         960
                       *     *     *     *     *     *     *     *     *     *     *     *
BOVINE PGE    CCCACACCTC CCATCTACAA TTTAACAGCC ATGAATGTCC CAATTGCAGT ATGGAGTGCT>
              ^^^^^^^^^^ ^^^^^^^^^^ ^^^^^^^^^^ ^^^^^^^^^^ ^^^^^^^^^^ ^^^^^^^^^^
KID PGE       CCCACACCTC CCATCTACAA TTTAACAGCC ATGAATGTCC CAATTGCAGT ATGGAGTGCT 970         980         990        1000        1010        1020
                       *     *     *     *     *     *     *     *     *     *     *     *
BOVINE PGE    GaCaAtGACC TGTTGGCTGA CCCTCAGGAT GTTGACtTTc TGCTTTCAAA ACTCTCTAAT>
              ^_^^_^_^^^^ ^^^^^^^^^^ ^^^^^^^^^^ ^^^^^^_^^_ ^^^^^^^^^^ ^^^^^^^^^^
KID PGE       GGCCAAGACC TGTTGGCTGA CCCTCAGGAT GTTGACCTTT TGCTTTCAAA ACTCTCTAAT
```

FIG. 2(B)

```
              1030       1040       1050       1060       1070       1080
               *    *     *    *     *    *     *    *     *    *     *    *
BOVINE PGE  CTCATTtACC ACAAGGAAAT TCCAAATTAC AATCACtTGG ACTTTATCTG GGCAATGGAT>
            ^^^^^^_^^^ ^^^^^^^^^^ ^^^^^^^^^^ ^^^^^__^^^ ^^^^^^^^^^ ^^^^^^^^^^
KID PGE.    CTCATTCACC ACAAGGAAAT TCCAAATTAC AATCATCTGG ACTTTATCTG GGCAATGGAT 1090       1100       1110       1120       1130
               *    *     *    *     *    *     *    *     *    *
BOVINE PGE  GCACCTCAAG AAGTTTACAA TGAAATTgTT TCTTTGATGG CcgAAGACAA AAAG>
            ^^^^^^^^^^ ^^^^^^^^^^ ^^^^^^_^^ ^^^^^^^^^^ ^__^^^^^^^ ^^^^
KID PGE     GCACCTCAAG AAGTTTACAA TGAAATTATT TCTTTGATGG CAAAAGACAA AAAG
```

FIG. 2(C)

PGE AMINO ACID/CODON SUMMARY

Tryptic Digest Fragment

--ASP-VAL-TYR-VAL-ALA-HIS-ASN-PRO-ALA-GLY-THR-SER-VAL-GLN-ASN-ILE-LEU-HIS--

Possible Codons:

```
  2   4   2   4   4   2   2   4   4   4   4   6   4   2   2   3   6   2

--GAC-GTA-TAT-GTA-GCA-CAT-AAT-CCA-GCA-GGA-ACA-TCA-GTA-CAA-AAC-ATA-CTA-CAT--
   T   C   C   C   C   C   C   C   C   C   C   C   C   G   T   C   C   C
       T       T   T               T   T   T   T   T   T           T   T
       G       G   G               G   G   G   G   G   G               G
                                               AGC                     TTA
                                                 T                      G
```

Tryptic Digest Fragment

--ASN-ALA-LEU-PHE-ALA-ILE-THR-GLY-ALA-ASP-ASN-LYS--

Possible Codons:

```
  2   4   6   2   4   3   4   4   4   2   2   2

AAC-GCA-CTA-TTC-GCA-ATA-ACA-GGA-GCA-GAC-AAC-AAA
 T   C   C   T   C   C   C   C   C   T   T   G
     T   T       T   T   T   T   T
     G   G       G   T   G   G   G
         TTA
          G
```

FIG. 3

| | | | | |
|---|---|---|---|---|
| Definition | lipase | | | |
| Coding region | note: gastric lipase. | | gi\|344241: | 47..1243 |
| Protein | Name: lipase | | gi\|344242: | [ Whole ] |
| NCBI | Seq ID: 344242 | | | |
| Method | conceptual translation | | | |
| Sequence | 398 aa | | | |

```
     —signal peptide—→                                    ①
   1 mwllltmasl isvlgtthgl fgklhpgspe vtmnisqmit/ywgypneeye
  51 vvtedgyile vnripygkkn sgntgqrpvv flqhgllasa tnwisnlpnn
 101 slafiladag ydvwlcnsrg ntwarrnlyy spdsvefwaf sfdemakydl
 151 patidfivkk tgqkqlhyvq hsqgttigfi afstnpslak riktfyalap
 201 vatvkytksl inklrfvpqs lfkfifgdki fyphnffdqf latevcsrem
         ②              ④                              ③
 251 lnllcsnalf iicgfdsknf ntsrldvyls hnpagtsvcn/mfhwtqavks
 301 gkfqaydwgs pvqnrmhydq sqppyynvta mnvpiavwng gkdlladpqd
 351 vglllpklpn liyhkeipfy nhldfiwamd apqevyndiv smisedkk
```

☐
highly conserved
hexapeptide
Gorqourri etal.
1989 88A 1006: 255

☐ ↗
Presumed catalytic
site homology

FIG. 5

Free fatty acid extraction set up

Typical chromatogram of free fatty acid standard

Free Fatty Acid (FFA) Profile of Kid Pregastric Esterase (KPGE) from Lipolyzed Butter Oil

Outline of the Procedure 2.1. Clone the gene of interest into one of the three *Pichia* Expression Vectors (see Section 5.4).

2.2. Perform a transformation (see Section 6.2).

2.2.1. Linearize the resulting construct by digestion with *Not* I or *Bgl* II (see Section 6.2.1).

2.2.2. Prepare spheroplasts of *his4 Pichia pastoris* strain GS115. Transform spheroplasts with the linearized construct (see Section 6.2.3).

2.2.3. A recombination event occurs *in vivo* between the 5' and 3' *AOX1* sequences in the *Pichia pastoris* vector and those in the genome. This results in the replacement of the *AOX1* gene with the gene of interest.

The *Pichia pastoris* genome now contains the gene of interest and the *HIS4* gene.

2.2.4. Plate transformants on histidine-deficient media. Cells in which recombination has occurred will grow, others will not produce histidine and will die (see Section 6.2.5).

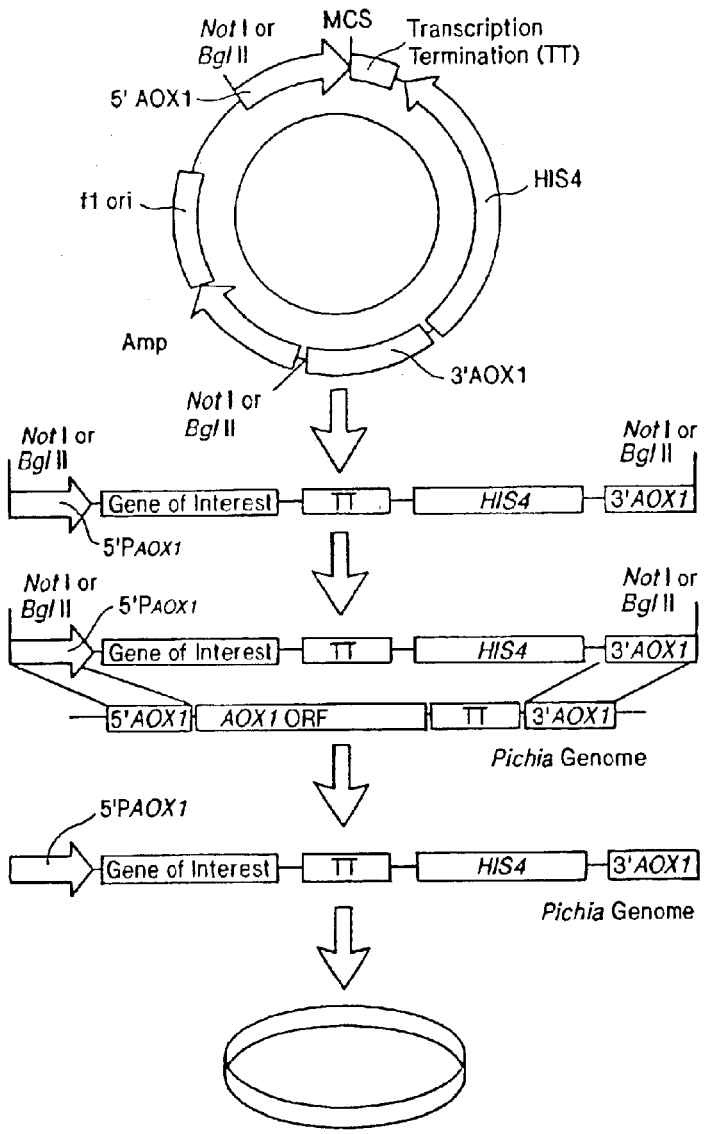

FIG. 11(A)

Outline of the Procedure (cont)

2.3. Screen for Recombinant Strain (see Section 6.3).

2.3.1. Screen for Integration at the correct loci. Select colonies from the -his plate and patch onto a -his, +glycerol and a -his, +methanol plate. Colonies which grow slowly on the -his, +met plate no longer contain the *AOX1* gene and have a his+, mut- (methanol utilization deficient) phenotype.

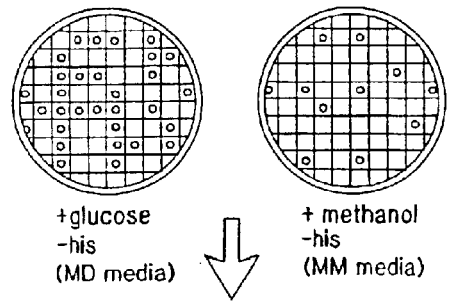

+glycerol  
-his  
(MD media)

+ methanol  
-his  
(MM media)

2.4. Pilot Expression (see Sections 6.4-6.6).

2.4.1. Select 10-20 his+, mut- colonies and grow for 2 days in media containing glycerol as the carbon source (see Sections 6.4 & 6.5).

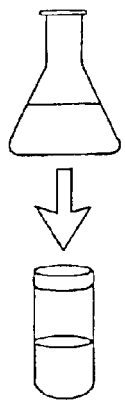

2.4.2. Pellet the cells and remove the media.

2.4.3. To induce expression, resuspend pellet in media containing methanol as the carbon source. Grow cells for 2-6 days.

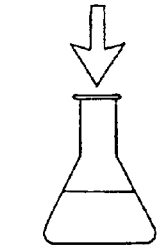

2.4.4. Analyze protein expression by SDS-PAGE and Western blot (see Section 6.6).

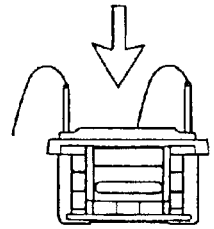

2.5. Scale up expression.

FIG. 11(B)

RECOMBINANT KID PREGASTRIC ESTERASE AND METHODS FOR ITS PRODUCTION AND USE

This application is a divisional of U.S. Ser. No. 10/043,665, filed on Jan. 14, 2002, now U.S. Pat. No. 6,582,948, which is a divisional of U.S. Ser. No. 09/186,489 filed on Nov. 5, 1998, now U.S. Pat. No. 6,375,947, issued on Apr. 23, 2002, the contents hereby incorporated by reference as if set forth in its entirety.

Throughout this specification, various references are identified by a number in parantheses. The citation to the reference corresponding to the identified number can be found in the section entitled References Cited preceding the claims. The references in that section are hereby incorporated by reference.

BACKGROUND OF THE INVENTION

Esterases (also referred to as lipases) are enzymes that cleave triglycerides (fats or lipids) or esters into carboxylic acids (fatty acids) and mono- and di-glycerides. For an explanation of the slightly different definitions given to lipases and esterases see Siezen, R. J. and van den Berg, (37). A pregastric esterase is an esterolytic or lipolytic enzyme secreted by the oral tissues of mammals. Animal esterases in an unpurified form called rennet have been used in the production of dairy food products and, in particular, the production of enzyme modified cheeses or EMCs. (8), (9), (10), (17), (18), (33), (40), and (41). In particular, cheeses like Romano and Provolone have a "peppery" or "piccante" flavor due to the fatty acid composition created by the enzyme in the rennet paste. (26), (37).

Traditionally EMCs are prepared by esterases obtained from the gullet of slaughtered animals from which a rennet paste or powder is obtained. The rennet is used to treat whey to impart flavor into the cheese product. Kid pregastric estersase (kPGE or kid PGE) in rennet paste is contaminated with proteins which are found in the gullet of the kid and other substances used in the preparation of the rennet. It would be useful to have an uncontaminated kPGE to produce EMC's. Such EMC's could be produced in a manner acceptable to kosher and vegetarian consumers. A recombinant kPGE (rKPGE) could be produced in very pure form free of the other substances found in the present commercial rennet formulations.

SUMMARY OF THE INVENTION

The present invention provides kPGE and derivative polypeptides which are capable of being produced by genetic recombination and used to produce EMCs. This invention further provides nucleic acid sequences encoding kPGE and derivative polypeptides which can be used to create recombinant host cells that express kPGE and derivative polypeptides. A further subject of the present of invention is a fusion polypeptide called polyHis-enterokinase which increases expression of esterases and lipases when fused to the N-terminal of the esterase or lipase. This invention also provides a method for treating animals with an esterase or lipase deficiency by administering rkPGE to the animal in a therapeutically effective amount.

BRIEF DESCRIPTION OF THE DRAWINGS

FIG. 1 is a comparison of an amino acid sequence for kid pregastric esterase to the amino acid sequences of bovine gastric esterase, human gastric lipase and rat lingual lipase.

FIGS. 2(A), 2(B), and 2(C) are a comparison of the genes encoding kid and bovine pregastric esterase.

FIG. 3 is an amino acid and codon summary for the isolated kid pregastric esterase corresponding to the N-terminal sequence.

FIG. 5 is the amino acid sequence for human gastric lipase in single letter form and homologous regions of the corresponding kPGE partial amino acid sequences are indicated.

FIGS. 11(A) and 11(B) depict the procedure for expression of kPGE in the *Pichia* expression system. FIG. 11(A) Clone the gene of interest into one of the *Pichia* expression vectors. Perform a transformation of the expression vector. Linearize the resulting construct by digestion with Not I or BgI II. Prepare sphereoplasts of his4 *Pichia pastoris* strain GS115 then transform the spheroplasts with the linearized construct. Recombination occurs in vivo between the 5' and 3' AOX1 sequences in the *Pichia pastoris* vector and those in the genome. This results in the replacement of the AOX1 gene with the kidPGE gene. The *Pichia pastoris* genome now contains the kPGE and the HIS4 gene. Transformants are plated on histidine-deficient media. Cells in which recombinantion has occurred will grow, others will not produce histidine and will die.

FIG. 11(B) depicts screening for a recombinant strain expressing the kPGE gene. Screen for integration at the correct loci. Select colonies from the –his plaste and patch onto a –his,+glycerol and a –his,+methanol plate. Colonies which grow slowly on the –his,+met plate no longer contain the AOX1 gene and have a his+,mut– (methanol utilization deficient) phenotype. Pilot expression can now occur by selecting 10–20 his+,mut– colonies and grow for two days in media containing glycerol as the carbon source. Pellet the cells and remove the media. To induce expression, resuspend pellet in media containg methanol as the carbon source and grow the cells for 2–6 days. Analyze protein expression by SDS-PAGE and Western blot techniques. Based on the pilot expression results, expression can be scaled up.

DETAILED DESCRIPTION OF THE INVENTION

Figure 4:
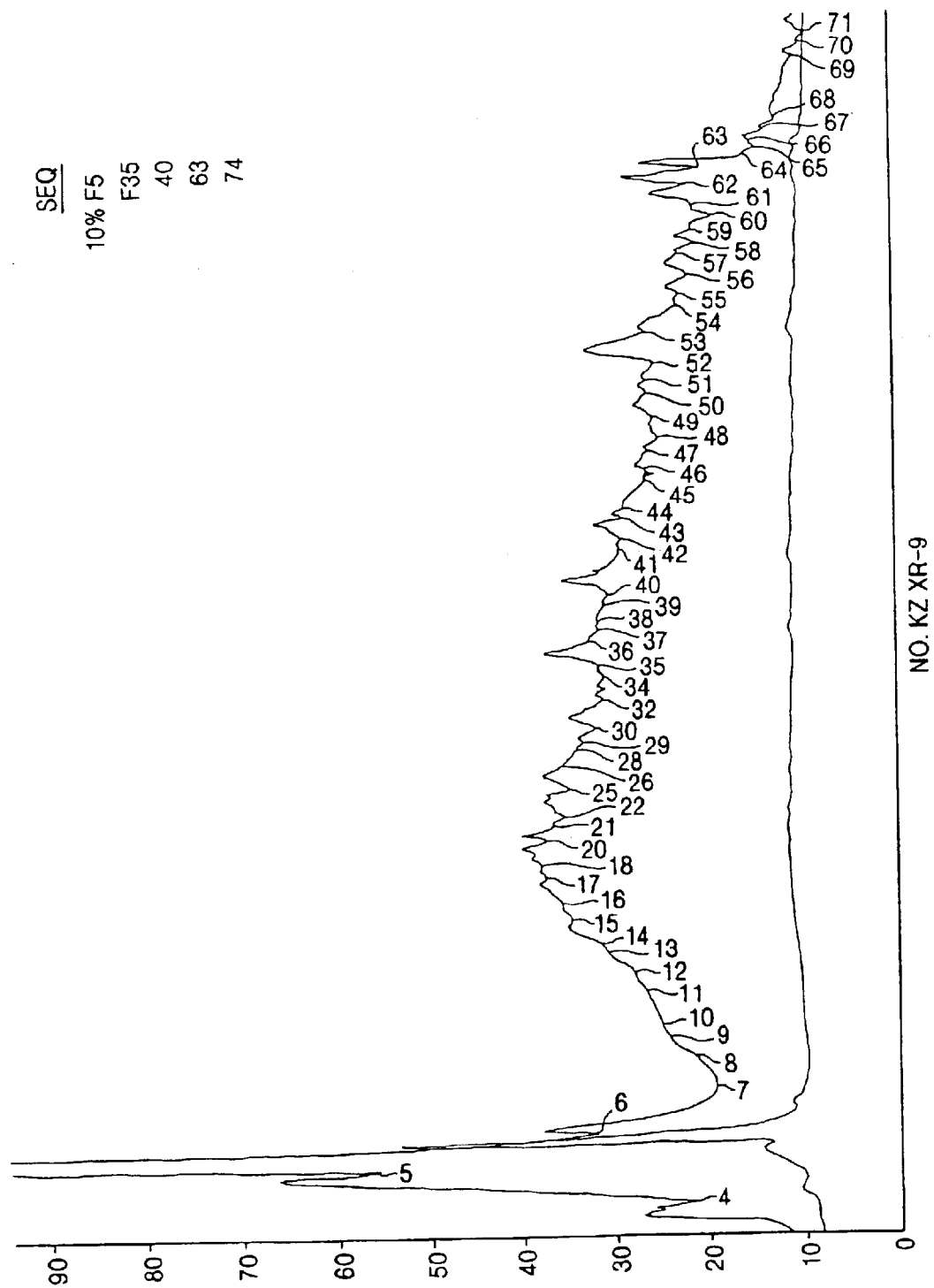
FIG. 4 is the HPLC separation purified fragments collected as individual species corresponding to 210 nm absorbance peaks.

The term "kPGE" refers to kid pregastric esterase. The term "rkPGE" refers to recombinant kid pregastric esterase. Kid pregastric esterase includes alleles of naturally occurring kid pregastric esterase. KPGE is an enzyme that is capable of producing a carboylic acid mixture from in about the same mixture as a commercial kid rennet preparation. A polypeptide derivative of kPGE is capable of the same function as kPGE but differs in the amino acid sequence of kPGE in at least one of the ways described below.

Derivatives of kPGE can differ from naturally occurring kPGE in amino acid sequence or in ways that do not involve sequence, or both. Derivatives in amino acid sequence are produced when one or more amino acids in naturally occurring kPGE is substituted with a different natural amino acid, an amino acid derivative or non-native amino acid. Particularly preferred embodiments include naturally occurring kPGE, or biologically active fragments of naturally occurring kPGE, whose sequences differ from the wild type sequence by one or more conservative amino acid substitutions, which typically have minimal influence on the secondary structure and hydrophobic nature of the protein or peptide. Derivatives may also have sequences which differ by one or more non-conservative amino acid substitutions, deletions or insertions which do not abolish the kPGE biological activity. Conservative substitutions (substituents) typically include the substitution of one amino acid for another with similar characteristics such as substitutions within the following groups: valine, glycine; glycine, alanine; valine, isoleucine; aspartic acid, glutamic acid; asparagine, glutamine; serine, threonine; lysine, arginine; and phenylalanine, tyrosine. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid.

Other conservative substitutions can be taken from Table 1, and yet others are described by Dayhoff in the Atlas of Protein Sequence and Structure (1988).

TABLE 1

Conservative Amino Acid Replacements

| For Amino Acid | Code | Replace with any of |
|---|---|---|
| Alanine | A | D-Ala, Gly, beta-ALa, L-Cys, D-Cys |
| Arginine | R | D-Arg, Lys, homo-Arg, D-homo-Arg, Met, D-Met, Ile, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Beta-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val, Norleu |
| Phenylalanine | F | D-Phe, Tyr, D-Thr, L-Dopa, His, D-His, Trp, D-Trp, Trans 3, 4 or 5-phenylproline, cis 3, 4 or 5 phenylproline |
| Proline | P | D-Pro, L-I-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), Val, D-Val |
| Threonine | T | D-Thr, Ser, D-Ser, allo-Thr, Met, D-Met, Met(O) D-Met(O), Val, D-Val |

TABLE 1-continued

Conservative Amino Acid Replacements

| For Amino Acid | Code | Replace with any of |
|---|---|---|
| Tryrosine | Y | D-Tyr, Phe, D-Phe, L-Dopa, His, D-His |
| Valine | V | D-Val, Leu, D-Leu, Ile, D-Ile, Met, D-Met |

Other derivatives within the invention are those with modifications which increase peptide stability. Such derivatives may contain, for example, one or more non-peptide bonds (which replace the peptide bonds) in the peptide sequence. Also included are: derivatives that include residues other than naturally occurring L-amino acids, such as D-amino acids or non-naturally occurring or synthetic amino acids such as beta or gamma amino acids and cyclic derivatives. Incorporation of D- instead of L-amino acids into the polypeptide may increase its resistance to proteases. See, e.g., U.S. Pat. No. 5,219,990, incorporated by reference herein.

The polypeptides of this invention may also be modified by various changes such as insertions, deletions and substitutions, either conservative or nonconservative where such changes might provide for certain advantages in their use.

In other embodiments, derivatives with amino acid substitutions which are less conservative may also result in desired derivatives, e.g., by causing changes in charge, conformation and other biological properties. Such substitutions would include for example, substitution of hydrophilic residue for a hydrophobic residue, substitution of a cysteine or proline for another residue, substitution of a residue having a small side chain for a residue having a bulky side chain or substitution of a residue having a net positive charge for a residue having a net negative charge. When the result of a given substitution cannot be predicted with certainty, the derivatives may be readily assayed according to the methods disclosed herein to determine the presence or absence of the desired characteristics.

Derivatives within the scope of the invention include proteins and peptides with amino acid sequences having at least eighty percent homology with kPGE. More preferably the sequence homology is at least ninety percent, or at least ninety-five percent.

Just as it is possible to replace substituents of the scaffold, it is also possible to substitute functional groups which decorate the scaffold with groups characterized by similar features. These substitutions will initially be conservative, i.e., the replacement group will have approximately the same size, shape, hydrophobicity and charge as the original group. Non-sequence modifications may include, for example, in vivo or in vitro chemical derivatization of portions of naturally occurring kPGE, as well as changes in acetylation, methylation, phosphorylation, carboxylation or glycosylation.

In a further embodiment the protein is modified by chemical modifications in which activity is preserved. For example, the proteins may be amidated, sulfated, singly or multiply halogenated, alkylated, carboxylated, or phosphorylated. The protein may also be singly or multiply acylated, such as with an acetyl group, with a farnesyl moiety, or with a fatty acid, which may be saturated, monounsaturated or polyunsaturated. The fatty acid may also be singly or multiply fluorinated. The invention also includes methionine analogs of the protein, for example the methionine sulfone and methionine sulfoxide analogs. The invention also includes salts of the proteins, such as ammonium salts, including alkyl or aryl ammonium salts, sulfate, hydrogen sulfate, phosphate, hydrogen phosphate, dihydrogen phosphate, thiosulfate, carbonate, bicarbonate, benzoate, sulfonate, thiosulfonate, mesylate, ethyl sulfonate and benzensulfonate salts.

Derivatives of kPGE may also include peptidomimetics of kPGE. Such compounds are well known to those of skill in the art and are produced through the substitution of certain R groups or amino acids in the protein with non-physiological, non-natural replacements. Such substitutions may increase the stability of such compound beyond that of the naturally occurring compound.

A yeast strain comprising a recombinant DNA molecule which expresses kid pregastric esterase was deposited with the Northern Regional Research Center and received deposit no. NRRL Y-30030.

It will be appreciated from the present disclosure that the kid pregastric esterase and derivatives and fatty acid mixtures according to the present invention can be used to alter, vary, fortify modify, enhance or otherwise improve the taste of a wide variety of materials which are ingested, consumed or otherwise organoleptically sensed.

The terms "alter" and "modify" in their various forms will be understood herein to mean the supplying or imparting of a flavor character or note to an otherwise bland, relatively tasteless substance, or augmenting an existing flavor characteristic where the natural flavor is deficient in some regard or supplementing the existing flavor impression to modify its organoleptic character.

The term "enhance" is intended herein to mean the intensification (by the use of the kid pregastric esterase and derivatives of the present invention) of a flavor or aroma note or nuance in a foodstuff or dairy product or cheese without changing the quality of said note or nuance.

The term "flavoring composition" is taken to mean one which contributes a part of the overall flavor impression by supplementing or fortifying a natural or artificial flavor in a material or one which supplies substantially all the flavor and/or aroma character to a consumable article.

The term "foodstuff" as used herein includes both solid and liquid ingestible materials for man or animals which materials usually do, but need not, have nutritional value. Thus, foodstuffs include meats, gravies, soups, convenience foods, malt, alcoholic, milk and dairy products, seafoods, candies, vegetables, animal foods, veterinary products and the like. The kid pregastric esterase and derivatives of the present invention are useful in the creation of flavor in cheeses or cheesefoods or any other food containing triglycerides.

The carboxylic acid mixture produced by the kid pregastric esterase and derivatives of the present invention can be combined with conventional flavoring agents or adjuvants. Such co-ingredients or flavor adjuvants are well known in the art for such and have been extensively described in the literature. Requirements of such adjuvants are: (1) that they be non-reactive with the carboxylic acid mixture of the present invention; (2) that they be organoleptically compatible with the mixture of the present invention such that the flavor of the mixture is not adversely affected by the use of the adjuvant; and (3) that they be ingestibly acceptable and thus non-toxic or otherwise non-deleterious. Appart from these requirements, conventional materials can be used and broadly include other flavor materials, vehicles, stabilizers, thickeners, surface active agents, conditioners, and flavor intensifiers.

The following terms are used in accordance with their meanings in the art. DNA is deoxyribonucleic acid whether single- or double-stranded. Complementary DNA (cDNA) is DNA which has a nucleic acid sequence obtained from reverse transcription of messenger ribonucleic acid (mRNA). Recombinant genetic expression refers to the methods by which a DNA molecule encoding a polypeptide of interest is used to transform a host cell so that the host cell will express the polypeptide of interest. A plasmid or vector can be used to introduce a DNA molecule into a host cell. A plasmid or vector can comprise, but need not, in addition to the gene or nucleic acid sequence of interest, a gene that expresses a selectable marker or phenotype and a gene that can control (induce or inhibit) the expression of the gene of interest under certain conditions.

This invention comprises a kid pregastric esterase which is free of other kid proteins. The kPGE can be produced by purifying the kid pregastric esterase from kid gullet or by recombinant genetic expression in a non-kid cell. The non-kid cell can be a bacterial, a fungal, a yeast or an animal cell. In a preferred embodiment, the yeast is *Saccharomyces cerevisiae*. The bacterial cell *E. Coli* can be used as can the Chinese Hamster Ovary cell. In the invention, the kid pregastric esterase have glycosylation which is different than that of kid pregastric esterase produced in a kid cell.

The present invention further provides a polypeptide comprising an amino acid sequence addition, substitution, or deletion derivative of kid pregastric esterase wherein the polypeptide is capable of converting fats to fatty acids in about the same ratio as kid pregastric esterase is capable of converting.

The ratio of fatty acids the polypeptide derivative is capable of converting has about the same flavor as would a ratio of fatty acids converted by kid pregastric esterase and the fats capable of being converted are from a dairy product. In one embodiment, a polyHis-enterokinase is added to the N-terminal of the amino acid sequence of kid pregastric esterase. The polyHis-enterokinase can have the amino acid sequence in SEQ. ID. NO. 6.

The invention further provides a polyHis-enterokinase polypeptide. This polypeptide is capable of increasing lipase polypeptide expression when expressed at the N-terminal of the lipase polypeptide. In a further embodiment, the polyHis-enterokinase polypeptide comprises at least 5 His amino acids and can comprise the amino acid sequence in SEQ. ID. NO. 6.

The present invention provides isolated polynucleotides capable of expressing the polypeptides of the present invention. In one embodiment, the polynucleotide encodes an amino acid sequence of kid pregastric esterase or a derivative polypeptide of kPGE or a polypeptide which is complementary to the nucleic acid sequence of SEQ. ID. NO. 1. The polynucleotide can be DNA or RNA. The polynucleotide can comprise a nucleotide sequence encoding a polyHis-enterokinase polypeptide. In a further embodiment, the polynucleotide comprises the nucleic acid sequence of SEQ. ID. NO. 7.

The present invention provides a transforming nucleic acid molecule comprising a plasmid or vector comprising a nucleic acid sequence encoding the amino acid sequence of kid pregastric esterase or a derivative polypeptide. The transforming nucleic acid can comprise the nucleic acid sequence of SEQ. ID. NO. 5.

The present invention further provides cell capable of recombinantly expressing kid pregastric esterase or a polypeptide derivative of kPGE, wherein the cell has been tranformed with the nucleic acid encoding the expressable polypeptide. The cell can be a bacterial, a fungal, a yeast or an animal cell. In a preferred embodiment, the cell is the yeast cell Saccharomyces cerevisiae.

The present invention also provides a monoclonal antibody to the polypeptides of the subject invention.

The present invention discloses a process for recombinantly producing kid pregastric esterase by isolating a polynucleotide encoding an amino acid sequence for kid pregastric esterase; inserting the isolated polynucleotide into a vector or plasmid suitable to transform a host cell; transforming a host cell with the vector or plasmid comprising the isolated polynucleotide; and growing the transformed cells to express kid pregastric esterase.

The present invention teaches a method of treating an esterase deficient animal, wherein the animal is treated by administering a therapeutically effective amount of the kid pregastric esterase or derivative. In an embodiment, a pharmaceutical composition comprising a pharmaceutical carrier and a therapeutically effective amount of the kid pregastic esterase or a derivative.

The present invention discloses a mixture of fatty acids produced by reacting kid pregastric esterase with a dairy product. The the dairy product comprises lipolyzed butter oil, milk, cheese or whey. The present invention further discloses a process for producing a mixture of fatty acids comprising reacting a dairy product with a kid pregastric esterase. Thus, the kid pregastric esterase of the present invention is capable of being used in the production of EMC's as a substitute for a commercial rennet preparation and may be used in addition to such a preparation as well.

This invention will be better understood from the Experimental Details which follow. However, one skilled in the art will readily appreciate that the specific methods and results discussed are merely illustrative of the invention as described more fully in the claims which follow thereafter.

Experimental Details

Ultra Purification of kPGE Protein

A 250 ml 2.5×50 cm Bio-Rad Econo-column was packed with approximately 220 ml Bio-Rad Exchange Q chromotography matrix as specified by supplier. The column was washed (200 mls) and equilibrated in 50 mM Tris-Cl, pH 8.0 (=buffer).

Five grams of Aurotech Kid Pregastric Esterase (390 Ramsey Units) were brought up in 50 mM Tris-Cl, pH 8.0, mixed by stirring for approximately 20 min and centrifuged at 6500 rpm in a GAS rotor (7000 g) for 10 min. The supernatent was decanted and recentrifuged as before. Eighty mls was recovered and loaded into the column running at 2 mls/min.

The column was washed with buffer for 100 min. Initially the flow rate was 2 mls/min but this changed to approximately 1.5 mls/min by the end of this period. At 100 min, a 100 min linear gradient from 100% A=buffer to 100% B=1 M NaCl, 50 mM Tris-Cl, pH 8.0, was begun. Twenty five minutes into gradient, collection of fractions (2 min=3 mls) were begun and continued for 124 min. At 200 min, the gradient was held at 100% B for 50 min, they switched to 100% A and held 200 min to re-equilibrate the column.

Activity of the kPGE was assayed at 405 nm using p-nitrophenol buterate substrate. Twenty µl samples or dilutions are placed in microtiter dish wells and diluted with 180 µl of substrate solution prepared as follows: thirty mg of p-nitrophenol buterate is dissolved in 10 mls isopropanol and 1 ml added to 9 mls of 4.4% Triton X-100, 0.11% Gum Arabic, 50 mM Tris-Cl, pH 8 solution.

Fractions containing kPGE activity were pooled, diafiltered with 20 mM BIS-TRIS (bis[2-Hydrosyethyl]imino-tris[hydrosymethyl]methane) buffer, pH 7.1, and loaded onto a column containing 200 ml of PBE 94 chromatography gel (Pharmacia Biotech, Inc., Piscataway, N.J.) for chromatofocusing in the pH range of 9–4. The column was developed with a 1 to 10 dilution of Polbuffer 74 (Pharmacia Biotech, Inc., Piscataway, N.J.), pH 4.0. Fractions were collected and assayed at 405 nm using p-nitrophenol buterate substrate as described above. Fractions containing kPGE activity were pooled, concentrated and diafiltered against distilled water using a stirred cell device (Amicon, Inc., Beverly, Mass.), fitted with a high-flow, inert non-ionic membrane retaining 90% of molecules with molecular masses greater than 30,000 Daltons, i.e. PM30 (Amicon, Inc., Beverly, Mass.

Partially-purified and concentrated kPGE from the chromatofocusing column was subjected to electrophoresis in precast 12% polyacrylamide gels containing 375 mM Tris-Cl buffer, pH 8.8 (Bio-Rad Laboratories, Hercules, Calif.) to separate protein species from one another. Following separation, the kPGE protein species was localized to specific region of the gel by making horizontal cuts (~1 mm segments) along the length of the gel. This resulted in a continuous series of ~1 mm segments that contained protein species that had migrated at similar rates to end up in the same relative position in the gel. A small piece of each individual segment was macerated in Tris-Cl buffer, pH 8, and assayed for activity using p-nitrophenol buterate substrate as described above. Those acrylamide segments showing PGE activity were then macerated in buffer and subjected to electrophoresis in an electroelution devise (Isco, Inc. Lincoln Nebr.). In this manner, PGE activity was electroeluted and concentrated in buffer. PGE activity was reconfirmed using the p-nitrophenol buterate assay and electrophoresed in sodium dodecyl sulfate (SDS) to demonstrate recovery of an ~50,000 Dalton protein species. In addition, traditional Ramsey unit assays were conducted to verify that classical pregastric esterase (i.e. lipase) activity was recovered. The assay procedure follows the rate of change in pH that results from lipase acting on tributerin to release butyric acid. Combined lots of this ultra-purified kPGE were assayed for functionality.

Functionality Verification

Purified kPGE was assayed for a determination of lipolytic activity on milk butter fat and functionality evaluation in flavor modification.

Determination of Partial Amino Acid Sequences of kPGE and Demonstration of Homology of these Sequences to Other Preduodenal Lipase Enzymes Following native gel electrophoresis, proteins in the polyacrylamide gel were electrophoretically transferred to a polyvinylidenedifloride (PVDF) membrane support using the Western blot procedure. This procedure involves layering the gel between filter paper and immersing the entire gel in a tank filled with a buffer solution containing 25 mM Tris, 192 mM Glycine and 20% methanol. Two large electrodes on either side of the filter paper-gel-PVDF membrane sandwich allow horizontal electrophoretic transfer of the proteins in the gel to the PVDF membrane. Following transfer, brief staining of the PVDF membrane with Commassie Brilliant Blue R-250 (0.025% Commassie R-250 in 40% methanol; destained with 50% methanol) allowed recognition of the ultra-purified kPGE protein as a unique band. This unique protein band of ultra-purified kPGE was precisely trimmed from the PVDF membrane and subjected to N-terminal amino acid sequencing procedures to yield a partial N-terminal sequence. Multiple recoveries of similarly purified kPGE bands on PVDF supports were also subjected to protease digestion to release specific kPGE peptide fragments. The resulting fragment mixture was then subjected to HPLC separation, see FIG. 4, and the separated, purified fragments collected as individual species corresponding to 210 nm absorbance peaks. Individual fragment species were then subjected to N-terminal amino acid sequencing to obtain sequence data for three additional fragments internal to the kPGE protein. These sequences are presented in FIG. 3 along with corresponding potential DNA codons that can prescribe the amino acids in these peptide sequences.

A search of the NBRF protein database using these partial amino acid sequences led to the identification of high homology with regions of the human gastric lipase and rat lingual lipase. The amino acid sequence for human gastric lipase is shown in single letter form in FIG. 5 where homologous regions of the corresponding kPGE partial amino acid sequences are indicated.

Figure 6:
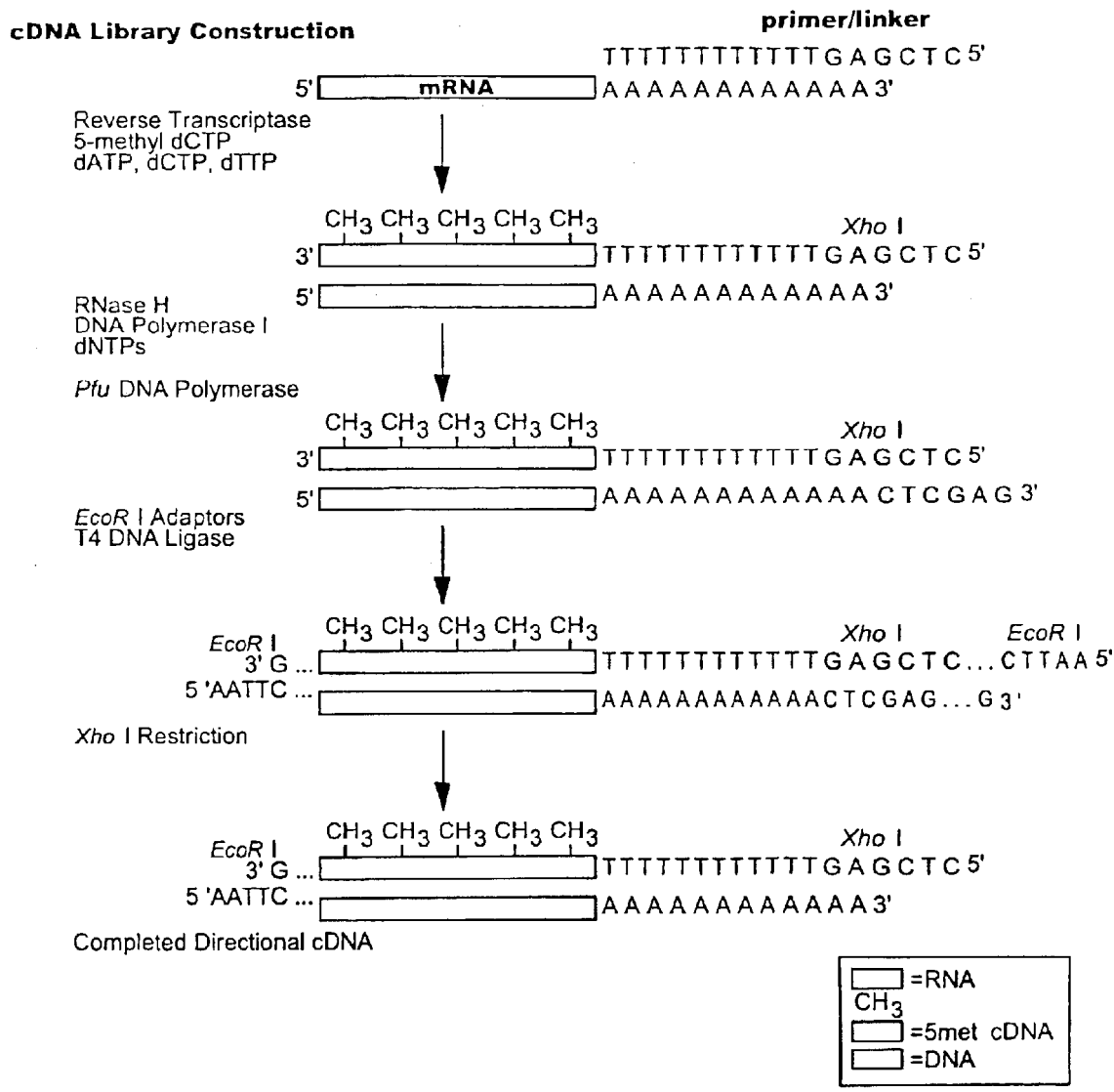
FIG. 6 shows a method for the construction of a cDNA library used to find the cDNA sequence for the kPGE gene.

Isolation of mRNA and Construction of CDNA Library of Cloned Sequences from Kid Lingual Tissue Frozen kid pregastric tissues, i.e. oral tissues known to produce lipolytic or esterolytic enzymatic activity, were homogenized in a lysis buffer (Tris-Cl, pH 8.0, LiCl, EDTA, Li dodecyl sulfate and dithiothreitol) polyadenylated messenger RNA (polyA-mRNA) isolated using a commercial product, Dynabeads Oligo (dT)25 (Dynal, Inc., Lake Success, N.Y.). In particular, polyA-mRNA was isolated from the parotid salivary glands and sublingual tissues of kid tongue, but other pregastric tissues for the lipolytic or esterolytic activity of interest as well. Purified polyA-mRNA was primed with an oligonucleotide consisting primarily of poly-deoxythymidine DNA and reverse transcribed into DNA using reverse transcriptase using procedures analogous to those outlined in FIG. 6. The resulting double-stranded DNA molecules were then cut with Eco R1 restriction enzyme and ligated into Eco R1-cut Lambda ZAP II vector DNA (Stratagene Cloning Systems, La Jolla, Calif.) to produce a library of Lambda ZAP II DNAs, each of which presumably contained one cDNA derived from one mRNA that was present in kid lingual tissue mRNA population. The library of cDNA-containing Lambda ZAP II DNAs was then packaged to form virulent bacteriophage using a commercially prepared packaging extract (Gigapack II gold packaging extract, Stratagene Cloning Systems, La Jolla, Calif.) and used to infect an appropriate strain of bacteria (XL1-Blue, Stratagene Cloning Systems, La Jolla, Calif.). Each infected cell contains only one type of Lambda ZAP II phage which replicates within the cell, directs the production of packaging components and becomes packaged to release many virulent phage (all identical in DNA structure) upon lysis of the cell. A primary phage library thus results that contains millions of virulent phage that comprise a population of phage, may of which contain cDNAs.

Development of Oligonucleotide Probes for Recognition and Recovery of the kPGE Gene from the cDNA Library From the kPGE amino acid sequences determined above, synthetic oligonucleotides were designed to be used in generating fragments of DNA that represent parts of the kPGE gene. Certain regions of the partial amino acid sequences were reverse translated into corresponding DNA sequences that would act as primers for DNA synthesis in the polymerase chain reaction (PCR). PCR techniques allow synthesis and amplification of regions of DNA that lie between two oligonucelotides (primers), one of which hybridizes to the plus strand and the other that hybridizes to the minus strand. Several rounds of synthesis lead to the generation of many copies of the fragment of DNA that lies between the two primers. The sequence of nucleotides found in the primers provides the specificity of the region of DNA that will be amplified. Since specific amino acids can be specified by more than one codon, mixtures of synthetic oligonucleotides were prepared that contained representatives of all possible sequences for the region of interest. These oligonucleotides were used in conjunction with similar oligonucleotides developed from conserved and homologous regions of similar enzymes, i.e. human gastric lipase, to synthesize segments of the kPGE gene using the PCR reaction. Since enzymes of this type, i.e. preduodenal lipases, are remarkably similar in size, ~50,000 Daltons, and the relative regions of homology of the partial kPGE amino acid sequences were known, the relative size of the expected DNA fragment from PCR synthesis with any two appropriate primers could be predicted. Thus, specific kPGE-based primers, conserved lipase-based primers or combinations thereof were used to carryout PCR using the library of cDNA-containing bacteriophage to generate specific DNA fragments. Several of these combinations yielded DNA fragment sizes expected to result from authentic kPGE gene sequences, but did not yield correctly sized DNA fragments if only the vector, i.e. Lambda ZAP II (not containing cDNA), DNA was used. In this way, the library was shown to contain DNA sequences of kPGE-like genes. DNA fragments generated from these PCR amplifications were cloned into a plasmid vector, pT7Blue T-vector (Novagen, Inc., Madison, Wis.) and transformed into bacterial cells (Novablue competent E. coli from Novagen, Inc., Madison, Wis.) using well-known bacterial transformation procedures. Each transformed cell, i.e. clone, contained many copies of one type of plasmid which contained a DNA fragment corresponding to a segment of a kPGE-like gene. Plasmid DNA preparations were made from several different transformed clones to recover larger quantities of purified DNAs containing different kPGE-like gene fragments. Several of these were DNA sequenced using common techniques and one (from clone GS 1972) was selected as clearly containing DNA sequence that when translated would produce a protein with very high amino acid sequence homology to comparable regions of other preduodenal and lingual lipases.

Identification and Recovery of the Cloned kPGE Gene from the cDNA Library

Plasmid DNA from a bacterial clone, i.e. GS 1972, was shown to consist of plasmid vector, pT7Blue T-vector (Novagen, Inc., Madison, Wis.), with an integrated PCR-generated DNA fragment (441 basepairs) corresponding to the translated region of amino acid residue ~18 to ~164 of other known, mature preduodenal and lingual lipases. This purified DNA was radioactively labeled with S35 by common procedures and used to identify phage carrying cDNAs with homologous regions by common screening procedures. Since the primary phage library contains millions of phage in a highly concentrated form, several rounds of phage purification must be conducted to separate the phage of interest, i.e. those containing kid-PGE-like cDNAs, from all others. Thus, semi-purified phage preparations were first identified by diluting the phage and planting on agar such that single phage plaques, i.e. a population of phage derived from only one phage, were clearly identified. Replicas of the phage plaque patterns that occurred on agar plates were then transferred to nitrocellulose membranes and probed with the radioactively labelled probe by common procedures to identify phage plaques of interest. Phage were then taken from the positive plaques on the agar plates and used to identify those that yielded an ~440 basepair fragment when amplified using the original primers in PCR experiments. Following initial identification of 10 positive semi-purified phage preparations, secondary and tertiary screens were performed as above to result in the identification of 5 highly-purified phage preparations that yielded a hybridizing signal when labeled with radioactive plasmid DNA from clone GS 1972 and an ~440 basepair fragment when amplified using the original primers in PCR experiments.

These 5 highly-purified phage preparations were then used to infect XL1 Blue cells (Stratagene Cloning Systems, La Jolla, Calif.) along with M13 helper phage to convert the cloned fragments from a phage form into a plasmid form, i.e. a phagemid. Proteins produced by the M13 helper phage cut the phage DNA on one side of the cloned insert DNA and replicate the DNA through to the other side. This smaller newly synthesized single-stranded DNA is then circularized, packaged and secreted from the cell. The secreted phagemid is then used to transform SOLR bacterial cells (Stratagene Cloning Systems, La Jolla, Calif.) along with another helper phage, VCSM13, to convert the phagemid into a replicating, stable plasmid. The SOLR cells are designed to prevent the replication of both M13 and Lambda phage such that only cells containing replicating plasmids are recovered when plated on an ampicillin-containing agar plate. In this way, 4 E. coli strains were obtained that contained pBluescript SK-doublestranded phagemids with cloned cDNA inserts of interest. DNA sequencing of the CDNA inserts of these phagemids, yielded a nucleotide sequence, a portion of which translated into a PGE-like enzyme. The translated sequence is comprised of 378 amino acids that form a protein with a calculated molecular mass of 42,687 Daltons. By comparison, human gastric lipase is comprised of 378 amino acids and has a calculated molecular mass of 43,208 Daltons; bovine pregastric esterase is comprised of 378 amino acids and has a calculated molecular mass of 42,987 Dalatons; while rat lingual lipase is comprised of 376 amino acids and has a calculated molecular mass of 42,700 Daltons. A comparison of the amino acid sequence alignments indicates the similarity among these enzyme, FIG. 1. At the DNA level, strong homology is still quite apparent, FIGS. 2(A–C). Inspection of the translated sequence of the PGE-like gene confirmed the presence of amino acid sequences that were determined above from the purified kPGE enzyme, thus confirming recovery of the kPGE gene. Expression of the kPGE in microorganisms and transgenic animals is possible with the nucleic acid sequence which can be used in recombinant genetic expression. A recombinant kPGE can fixed and delivered into food systems by spray drying or encapsulation. This kPGE, as the result of controlled synthesis and recovery of a highly purified form with natural lipase/esterase activity, is likely to be used to create new dairy flavors. Microbial production will allow the development of new Kosher and vegetarian food products.

Esterase Functionality Assay

All esterase samples were received frozen and stored in –18° C. freezer. Before being used, they were thawed and stored in 5° C. refrigerator. Original kid lipase, lot #81882, 390 U/gram samples: PGE SAMPLE 1; 0.6 ml at 5 U/ml in 20 mM phosphate buffer at pH 7.0; PGE SAMPLE 2: 0.6 ml at 5 U/ml in 20 mM phosphate buffer at pH 7.0; and PGE CONTROL: 0.6 ml in 20 mM phosphate buffer at pH 7.0. The substrate was 40% fat cream obtained from Golden Guernsey Dairy. Cream is free of added mono and diglyeride. All chemical reagents were obtained from Aldrich Chemical Company, Inc. and were the best grade available.

Usage level of all lipase samples are 0.78 U/gram of cream, which is comparable to the usage level in production. Samples are received in a capped 10 ml plastic tube. According to the usage level, 3.8 gram of cream is added into each tube. For the control, the lipase powder is dissolved in 20 mM phosphate buffer at pH 7.0 to the activity level of 5 Ramsey units per milliliter. Then, 0.6 ml of the solution is mixed with 3.8 grams of cream substrate in a capped plastic tube. They are incubated at 37° C. for 72 hours. At the end of incubation, no heat is applied because of small sample size. All samples are stored in a refrigerator until analysis.

Analysis
Titration

Each sample was titrated at the end of incubation. Because of the smaller sample size, titration could not be used to follow the fatty acid development. Take 0.1 gram sample from the flask and dissolve the sample with 50 ml isopropanol. Add 2–3 drops of phenolphthalein indicator and titrate it with 0.05 N NaOH till end point. Record the ml of 0.05 N NaOH used and convert to per gram basis.

Free Fatty Acid Profile

Free fatty acid profile of each sample was analyzed using the procedure below. This method quantify the following fatty acids: butyric, hexanoic, octanoic, decanoic, lauric, myristic, palmitic, palmitoleic, stearic, oleic, linoleic and linolenic acids. Results are expressed as mole percentage of the total free fatty acid. Because we did not have duplication due to limitation of enzyme samples, each sample was analyzed twice and results were averaged.

Organoleptic analysis

At the end of incubation, all enzyme samples have a different titration. A cheese sauce consisting of margarine, modified starch, and Velveeta cheese and water was used as the base for evaluation because it has been routinely used for evaluation of such samples. Since the samples had a different titration, the usage level of each on is varied to compensate for the titration variations.

Results

Total free fatty acids released by each enzyme preparation were quite different, even though the same amount of activity units were used in the incubation. The control lipase has the highest activity.

| SAMPLE | TITRATION (0.05 N NaOH/g) |
|---|---|
| Lipase control | 5.4 |
| PGE Sample 1 | 3.3 |
| PGE Sample 2 | 2.4 |
| PGE Control | 1.7 |

Unfortunately we did not have a plain cream control. It is possible that majority of the PGE control titration is from the milk lipase existing in the cream.

Free fatty acid profiles: The PGE Control shows a typical profile of milk lipase. The PGE sample 1 and the Lipase control have almost identical profiles. PGE sample 2 shows a different profile with much lower percentage in short chain fatty acids and higher percentage in long chain fatty acids. The overall activity of this sample is also much lower. The change of profile could be due to the impact of milk lipase in the system. When the lipase activity is low, impact of milk lipase could play a much bigger role. This might explain why the PGE sample 2 shows a different profile.

Organoleptic results: Because each sample has different titration, percentage of sample used in the cheese sauce for organoleptic evaluation varied depending on the sample strength:

| SAMPLE | PERCENTAGE USED |
|---|---|
| Lipase Control | 2.0 |
| PGE Sample 1 | 3.27 |
| PGE Sample 2 | 4.50 |
| PGE Control | 6.35 |

Overall, all these samples showed very similar organoleptic properties. They are not identified as typical fatty acid and had a culture milk type of flavor.

TABLE 3

Free fatty acid profile of lipase fractions

| FFA | CONTROL | PGE-S1 | PGE-S2 | PGE-CONTROL |
|---|---|---|---|---|
| C4:0 | 46.70 | 44.97 | 35.30 | 19.56 |
| C6:0 | 15.50 | 15.19 | 13.01 | 8.75 |
| C8:0 | 4.45 | 3.96 | 3.82 | 2.66 |
| C10:0 | 8.52 | 7.59 | 7.41 | 5.62 |
| C12:0 | 5.60 | 5.16 | 5.00 | 4.71 |
| C14:0 | 5.34 | 5.93 | 7.09 | 10.74 |
| C16:0 | 5.55 | 8.42 | 13.63 | 23.88 |
| C16:1 | 1.11 | 1.00 | 1.69 | 2.93 |
| C18:0 | 2.58 | 2.48 | 3.83 | 6.06 |
| C18:1 | 3.26 | 4.57 | 8.18 | 13.50 |
| C18:2 | 0.90 | 0.58 | 0.87 | 1.44 |
| C18:3 | 0.41 | 0.15 | 0.18 | 0.15 |

Assay Procedure for Lipase Activity

The substrate used is: 475 mL deionized water, 45 mL Tributyrin, 3 g Sodium Caseinate and 2.5 g Lecithin blended in a Waring blender. The pH was adjusted to 5.5 with 88% Lactic Acid and temperature 42° C.

An enzyme standard was created:
For Concentrate: 1 gram Standard in 99 mL of 3% NaCl; and
For Dilute: 10 gram Standard in 9.0 mL of 3% NaCl stirred in a tempered water bath at 42C for 15 min. The kid reference (400 R.U.'s) standard is 1:100 while the calf reference (68 R.U.'s) standard is 1:10.

Fill a 50 mL buret on a ring stand with 0.05N NaOH. Place 100 mL of substrate into a 250 Ml beaker and immerse a standardized pH electrode into the beaker. Place the beaker and electrode on a magnetic stir plate set at 3.8 to heat the sustrate to 42° C. while stirring constantly and adjust the pH to 5.5. Dispense 10 mL of Enzyme Standard Solution into the 250 mL beaker. Set the timer for 6 minutes and adjust the flow of NaOH to retain the pH at 5.5. Keep track of the amount of NaOH used the last 5 min. After 6 minutes has elapsed, close the buret and record the amount consumed.

Calculation

Calculate activity according to the following formulas:
Concentrate 1/100 Sample 1/100 (Kid) Sample 1/100 of Conc. Kid 1/10 of Cut Kid
(R.U.'s of control/Titer of control)×Titer of sample =Sample R.U.
Concentrate 1/100 Sample 1/10 (CALF)
(R.U.'s of control/Titer of control)×Titer of sample×1/10=Sample R.U.

Procedure for Extraction and Analysis of Free Fatty Acids from Lipolized and EMC Products This procedure extracts free fatty acids from lipolized butter and enzyme modified cheeses. The extract is then analyzed by gas chromatography method. This procedure is adapted from Deeth, H. C. et al. "A gas chromatography method for the quantitative determination of free fatty acid in milk and milk products" New Zealand Journal of Dairy Science and Technology, 18:13–20, which is hereby incorporated by reference. This procedure has been extensively tested for extraction efficiency. The adjustment for this procedure is the sample size which depends on the amount of free fatty acids in the sample. In Deeth et al., a packed GC column is used without further esterification. Here a bonded phase capillary tube is used to give a superior chromotogram compared to Deeth et al., especially for long chain fatty acids. Heptanoic acid is used as an internal standard for fatty acids with chain length of up to 10 carbons, while pentadecanoic acid is used for fatty acids with chain length of more than 12 carbons. In theory, one could use only one standard, for example heptanoic acid to do the calibration. The two internal standards used were chosen because very little of them exists in dairy products. The following reagents are used: necessary free fatty acids, isopropyl ether 99%, diethyl ether 99.9% (spectrophotometric grade), hexane (spectrophotometric grade), formic acid 96% (ACS reagent), activated aluminum oxide (acidic, Brockman I), 4N sulfuric acid, and glass wool treated with phosphoric acid.

This procedure uses a three level calibration for each fatty acid peak. However, it cannot quantify acetic acid in the product because formic acid used in the procedure contains small amounts of acetic acid which interferes with quantifying the acetic acid extracted from the sample.

Weigh the following amount of fatty acids into a 100 ml volumetric flask directly:

TABLE 4

| | Fatty Acid Levels | | |
|---|---|---|---|
| FATTY ACIDS | LEVEL 1 in mg | LEVEL 2 in mg | LEVEL 3 in mg |
| propionic acid | 50 | 50 | 50 |
| butyric acid | 50 | 50 | 50 |
| caproic acid | 50 | 50 | 50 |
| heptanoic acid (ISTD) | 60 | 40 | 20 |
| caprylic acid | 50 | 50 | 50 |
| capric acid | 50 | 50 | 50 |
| lauric acid | 50 | 50 | 50 |
| myristic acid | 50 | 50 | 50 |
| pentadecanoic (ISTD) | 60 | 40 | 20 |
| palrritic acid | 50 | 50 | 50 |
| palmitoleic acid | 50 | 50 | 50 |
| stearic acid | 50 | 50 | 50 |
| oleic acid | 50 | 50 | 50 |
| linoleic acid | 50 | 50 | 50 |
| linolenic acid | 50 | 50 | 50 |

Figure 8:
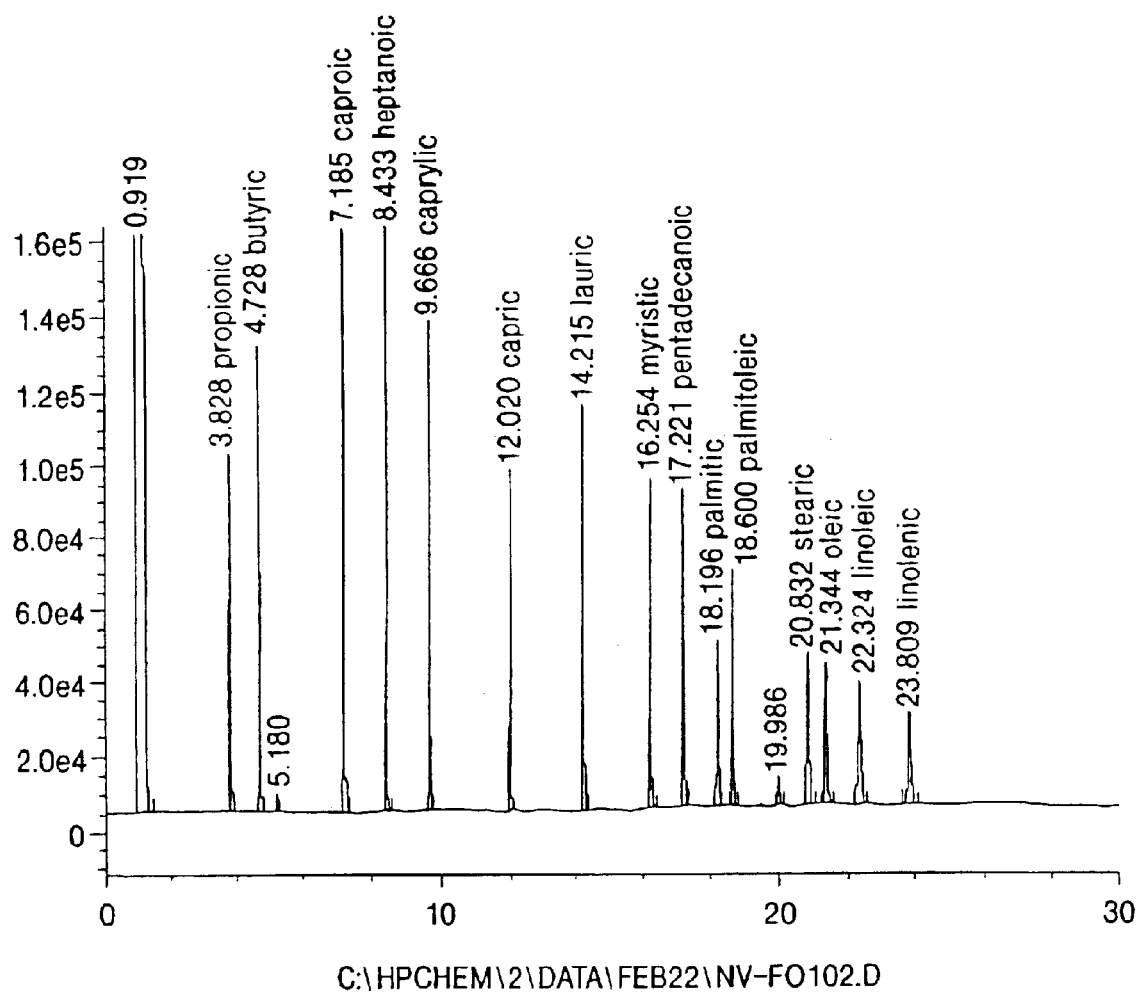
FIG. 8 is a typical chromatogram of a free fatty acid standard.
Figure 9:
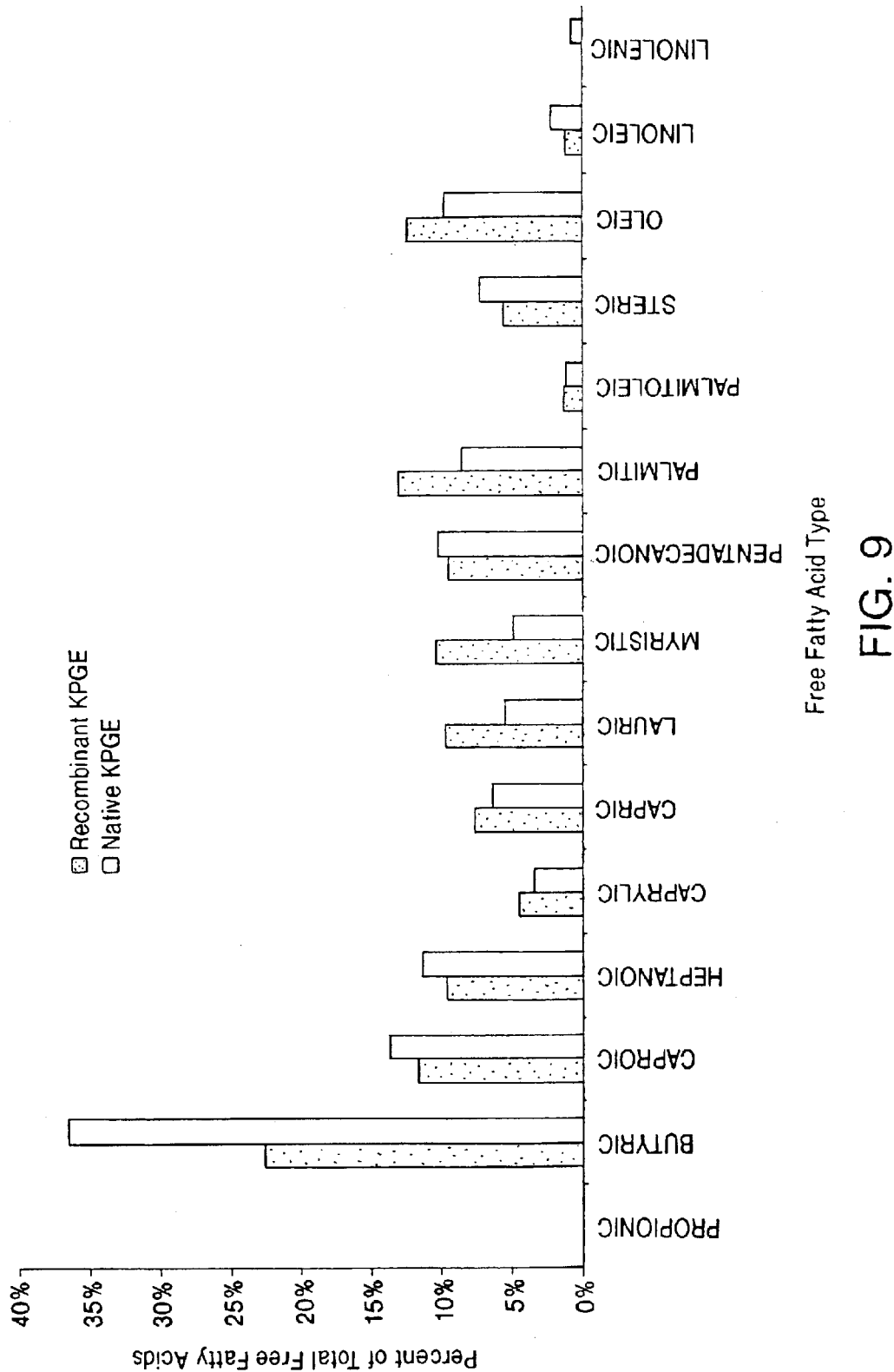
FIG. 9 is a comparison of the Free Fatty Acid (FFA) Profile of Kid Pregastric Esterase (KPGE) from Lipolyzed Butter Oil comparing the carboxylic acid mixture from lypolized butter oil using recombinant kid pregastric esterase and native kid pregastric esterase.
Figure 10:
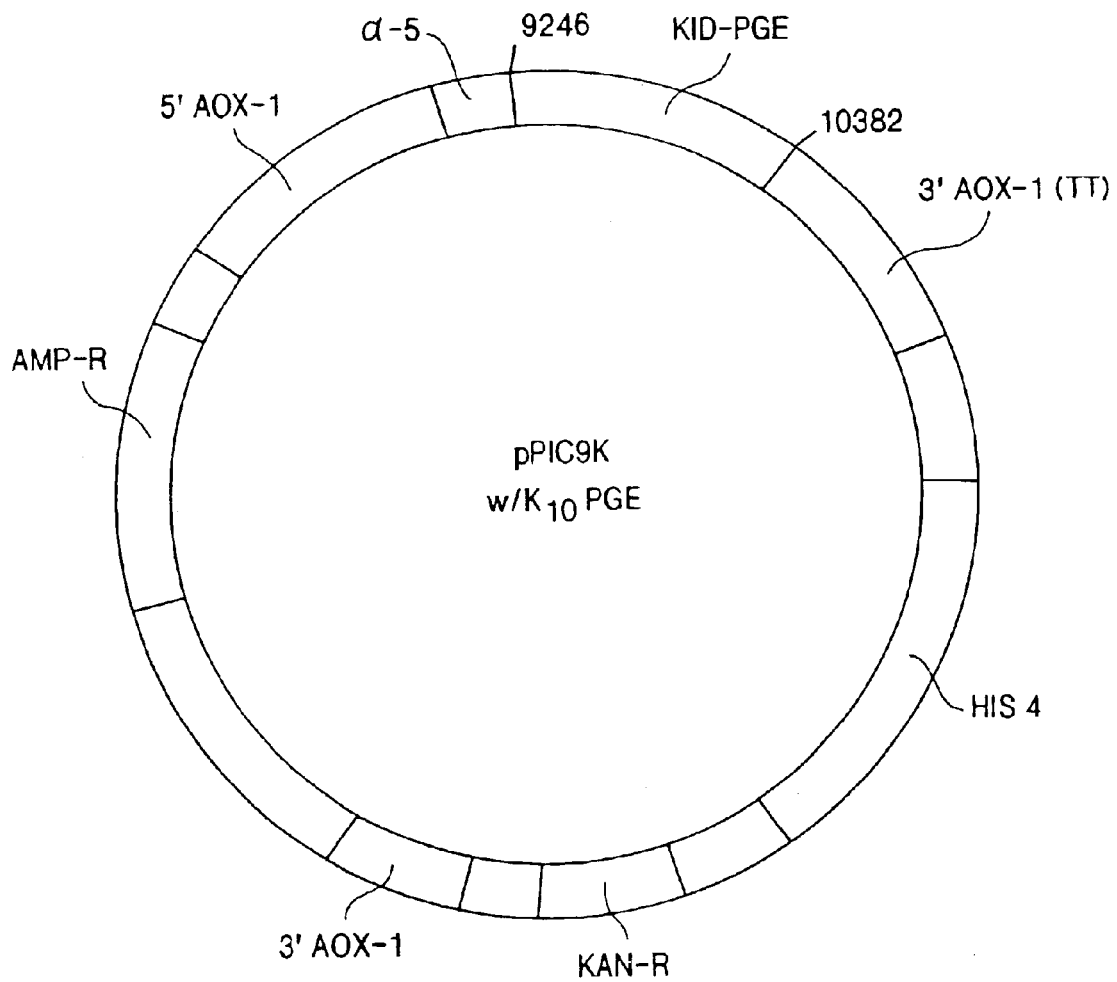
FIG. 10 is a shematic diagram of an expression vector (pPIC9K) with a sequence encoding kPGE.
Figure 12:
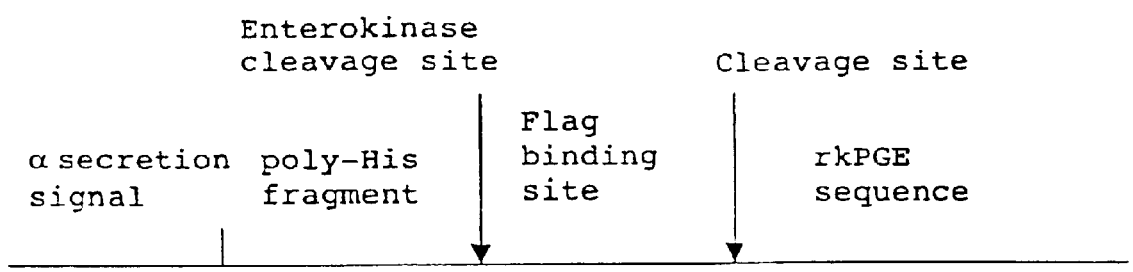
FIG. 12 schematically depicts a FLAG® expression sequence for kid pregastric esterase using the polyHis-enterokinase fusion polypeptide.

Use an analytical scale to weigh each compound and record to 0.1 mg. It is recommended that one starts weighing standards from the longer chain length fatty acids because they are less volatile. This will minimize loss due to evaporation. FIG. 8 shows a typical chromatogram of the standard. Note that retention time will vary depending on total length and column and condition of the column. Add 4 gram of formic acid into each flask. Fill each flask to mark with isopropyl either and mix well but exercise care to prevent leaking during mixing. Standard can be stored in small glass bottles (~10 ml) with Teflon® or other chemical resistant cap in freezer for future uses.

Preparation of Internal Standard (ISTD) Solution

Weigh about 0.3 gram of heptanoic acid and pentadecanoic acid into a 100 ml volumetric flask. Use and analytical scale for the weighing and record weight to 0.1 mg. Fill the flask with hexane till mark. Be sure the hexane is at room temperature. Mix well but exercise care to prevent leaking during mixing. Store internal standard solution in small glass bottles (~10 ml) with Teflon® or other chemical resistant cap in refrigerator for future uses. When it is to be used, be sure to let the bottle warm up to room temperature. Leaving the bottle at room temperature overnight is recommended.

Preparation of Column Packing

Deactivated alumina is used for adsorption of free fatty acids from the extract. Activated aluminum oxide, acidic, Brockmann I is used. It is deactivated according to the following steps. Preheat a drying oven to 225° C. Place about 20 grams alumina in a 100 ml beaker. Cover beaker with aluminum foil and make some holes on the foil with sharp needle. Place it into the heated oven. Each extraction uses about 1 gram of alumina. Dry it at this temperature for 2 hours. Stop heating of oven. Remove beaker and cool it in desiccator. Transfer to small wide-mouth bottle with screw cap. Close cap tightly. Record the powder dry weight. After dry powder is cool, add 4% water to deactivate the dry powder on the powder dry weight. Add water in four equal portions. Mix it very well with stainless steel spatula each time water is added until mixture is homogeneous. During this process, heat is released and the bottle should be warm. Cap it tightly and shake the bottle for 5 minutes. Store it in desiccator and equilibrate it at least overnight before using.

Extraction of Free Fatty Acids from Samples

This procedure is suitable for extracting free fatty acid from dairy products. The only difference for different samples will be the sample size. For samples with low degree of lipolysis, e.g., sample with about 4 ml 0.05 N NaOH free fatty acid titration per gram, use about 0.3 gram sample. For sample with strong lipolysis, such sample with free fatty acid titration of 16 ml 0.05 N NaOH per gram, use about 0.1 gram sample size. Caution: all extraction work has to be done in hood with good ventilation.

Make a solvent mix for extraction. It contains hexane/diethyl either at ration of 1:1 (vol:vol). Make enough to finish all extraction (about 35–40 ml for extraction). Weigh sample into a 50 ml centrifuge tube with screw cap. Caution: selection of centrifuge tube is very important because we are centrifuging ether at very high speed. Selecting the wrong type of centrifuge tube might create danger. Nelgene FEP oak ridge centrifuge tube with ETFE sealing cap assembly is selected because of its superior chemical compatibility. Add 0.1 ml of 4 N sulfuric acid into each tube. Add 0.100 ml of ISTD solution into each tube. Use a 0.2 ml glass pipet in 0.01 ml graduation to deliver the ISTD solution. Do not piper the solution with mouth. Calculate mg of internal standard compound added per gram of sample. This value is used for calculation during analysis according to the following formula:

$$\text{mg } ISTD/\text{g sample} = \frac{0.100 * ISTD \text{ conc. in mg/ml}}{\text{sample size in grams}}$$

Add 1 gram of anhydrous sodium sulfate into each tube. Add 10 ml of the extraction solvent form step 1 into each tube. Cap the tube tightly and mix it well with Vortex mixer at highest setting. Often the sample will dissolve in the extraction mixture. Extract it for 30 minutes to 1 hour. For lipolized butter samples which dissolve in extraction mixture easily, a 30 minute extraction is enough. For enzyme modified cheeses, extract it for about an hour. Make sure there is no lumping, use a small spatula to break any lumps.

Figure 7:
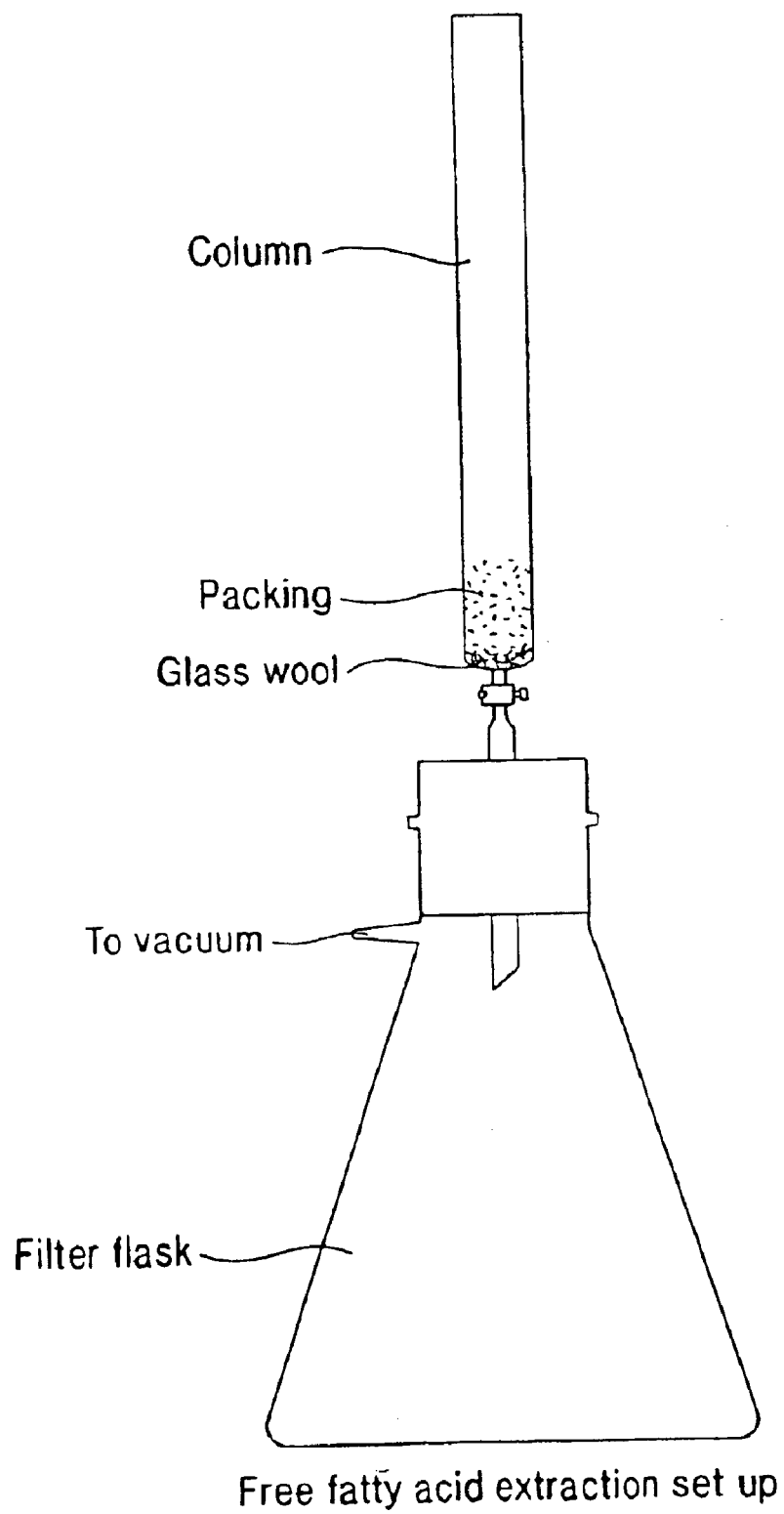
FIG. 7 depicts an extraction device for free fatty acids.

Centrifuge the tubes at 7000 rpm at 0° C. using Sorval SA-600 rotor for 5 minutes to obtain a clear supernatant which contains free fatty acids and fat. Be sure all the tubes are balanced before starting centrifugation. Pack a glass column with deactivated alumina. To do that, insert a small plug of acid treated glass wool into bottom of a 30 cm×11 mm chromatography column and than pack it with 1 gram of the deactivated alumina. Set up the column on a filter flask as shown in FIG. 7.

Carefully pour the supernatent from the centrifugation into a small glass beaker. Slowly introduce it into the column. Adjust the flow rate so that it drips slowly (about 0.5–1 drop/second). After all the extract passes through the column, wash the small beaker with liquid collected in the filter flask and pass it through the column again. Wash the column with 5 ml hexane/diethyl either mixture twice at the same flow rate as at (about about 0.5–1 drop/second). When introducing the solvent mixture into column, pour it slowly along the side of column so the solvent washes the column.

Start the vacuum slowly so when a finger is placed at the end of the vacuum hose, you can barely feel the suction. Connect the hose to filter flask to dry the alumina. Dry it till no lumping occurs when you tilt the column and the packing inside appears to be free flowing powder. Transfer the alumina into a small vial and cap tightly. Remove the glass wool from column. Wash the whole set up with extraction mixture so it will be ready for next sample. Column and flask can be blow-dried with air.

Prepare at 6.0% formic acid solution with isopropyl either. This is used to release fatty acid in the alumina packing. Weight 0.5 gram alumina from step 12 into a disposable microcentrifuge tube (1.5 ml capacity). Add 0.5 ml formic acid solution from step 14. Cap it and mix thorough. Let stand for abut 30 minutes with occasional mixing. Centrifuge it with MICROSPIN 12 centrifuge for 2 minutes to obtain clear supernatent. Transfer the supernatent into a 1 ml vial and cap it. This supernatent is ready for GC analysis.

Analysis of the Extract

The free fatty acid extract was analyzed by gas chromatograph (GC) method, using the following conditions:

| | |
|---|---|
| GC: | HP5890 II |
| Column: | HP-FFAP, 25 M × 32 mm with 0.52 um film thickness |
| Guard Column: | Restek capillary guard column, 5 M × 0.32 mm |
| Injector Temperature: | 28 C. |
| Detector Temperature | 300 C. |
| Oven Temperature: | 100 C.–240 C. at 8 C./min. |
| Initial Isothermal Time: | 0 Minutes |
| Final Isothermal Time: | 12.5 minutes |
| Total Analysis Time: | 30 minutes |
| Initial Inlet Pressure: | 20.0 psi |
| Constant Flow: | On |
| Flow Rate: | 3.7 ml/min |
| Split Flow: | 20.0 ml/min. |
| Detection: | FID |
| Injection: | 0.2 ul |

Stabilwax-DA 30 M×0.32 mm with 0.25 um film thickness from Restek can be also used with slightly less satisfaction for fatty acids with 18 carbon chain length.

Calculation of the Fatty Acids (mg) Per Gram of Product

The three levels of standard are analyzed with the same GC program. A calibration table is built containing three level linear calibration for each peak. After sample is analyzed, a report of mg/ml sample will be printed.

Calculating the Mol % of Fatty Acids per Gram of Product

To calculate the Mol % (Mol % is more useful for recognizing a fatty acid profile): calculate the mmole of each fatty acid per gram sample. To do that, divide the result of each fatty acid (unit: mg/g sample) by its molecular weight. Sum all the calculated mmole of each fatty acid per gram sample to obtain the total mmole of free fatty acid per gram of sample. Divide the mmole of each fatty acid per gram sample by the total mmole of free fatty acid per gram of sample. Multiple the calculated value by 100. This gives you the Mol %. To verify the calcualtion, the sum of the Mol % results of all fatty acids should total 100.

Expression Systems

General Characteristics of *Pichia pastoris*

The yeast *Pichia pastoris*, a microbial eukaryote, has been developed into a premier expression system. As a yeast, *Pichia pastoris* is as easy to use as *E. coli*, while having the advantages of eukaryotic expression (e.g. protein processing, folding, and posttranslational modifications). While possessing these advantages, it is faster, easier, and cheaper to use than other eukaryotic expression systems, such as baculovirus or mammalian tissue culture, and generally gives higher expression levels. *P. pastoris* is similar to the baker's yeast, *Saccharomyces cerevisiae*, including having the advantages of molecular and genetic manipulations, but with the added advantages of 10- to 100-fold higher heterologous protein expression levels and the protein processing characteristics of higher eukaryotes.

*Pichia pastoris* is completely amenable to the genetic, biochemical, and molecular biological techniques that have been developed over the past several decades for *S. cerevisiae* with little or no modification. In particular, transformation by complementation, gene disruption and gene replacement techniquest developed for *S. cerevisiae* work equally well for *Pichia pastoris*.

The genetic nomenclature adopted for *Pichia pastoris* mirrors that used for *S. cerevisiae* (unlike that of *Sc. pombe*). For example, the gene from *S. cerevisiae* that encodes the enzyme histidinol dehydrogenase is called the HIS4 gene and likewise the homologous gene from *Pichia pastoris* that encodes the same enzyme is called the *Pichia pastoris* HIS4 gene, and so on. there is a very high degree of cross-functionality between *Pichia pastoris* and *S. cerevisiae*. For instance, many *S. cerevisiae* genes have been shown to genetically complement the comparable mutants in *Pichia pastoris*, and vice versa (e.g. the *Pichia pastoris* HIS4 gene functionally complements *S. cerevisiae* his4 mutants and the *S. cerevisiae* HIS4 gene functionally complements *Pichia pastoris* his4 mutants; other cross-complementing genes that have been identified include LEU2, ARG4, TRP1, and URA3).

*Pichia pastoris* as a Methylotropic Yeast

*Pichia pastoris*, representing one of four different genera of methylotropic yeasts, which also include *Candida, Hansenula*, and *Torulopsis*, is capable of metabolizing methanol as a sole carbon source. The first step in the metabolism of methanol is the oxidation of methanol to formaldehyde by the enzyme alcoholoxidase. Expression of this enzyme, coded for by the AOX1 gene, is tightly regulated and induced by methanol to very high levels, typically ≧30% of the total soluble protein in cells grown with methanol as the carbon source. The AOX1 gene has been isolated and a plasmid-borne version of the AOX1 promoter is used to drive expression of the gene of interest for heterologous protein expression.

Expression of the AOX1 gene is controlled at the level of transcription. IN methanol grown cells approximately 5% of the polyA+ RNA is from the AOX1 gene. The regulation of the AOX1 gene is similar to the regulation of the GAL1 gene (and others) of *S. cerevisiae* in that control involves both a repression/derepression mechanism. However, unlike the situation in *S. cerevisiae*, derepression alone of the AOX1 gene (i.e. absence of a repressing carbon source such as glucose) is not sufficient to generate even minute levels of expression from the AOX1 gene. The inducer, methanol, is necessary for expression.

Use for Heterologous Protein Expression

*Pichia pastoris* has been used successfully to express a wide range of heterologous proteins. Heterologous expression in *Pichia pastoris* can be either intracellular or secreted. Secretion requires the presence of a signal sequence on the expressed protein to target it to the secretory pathway. While several different secretion signal sequences have been used successfully, including the native secretion signal present on some heterologous proteins, success has been variable. To improve the chances for success, two different vectors with different secretion signals are included in this kit: The vector, pHIL-S1, carries a native *Pichia pastoris* signal from the acid phosphatase gene, PHO1. The vector, pPIC9, carries the secretion signal from the *S. cerevisiae* mating factor pre-pro peptide.

Another advantage of expressing secreted proteins is that *Pichia pastoris* secretes very low levels of native proteins. that, combined with the very low amount of protein in the *Pichia* growth media, means that the secreted heterologous protein comprises the vast majority of the total protein in the media and serves as the first step in purification of the protein.

Like *S. cerevisiae*, linear DNA can generate stable transformants of *Pichia pastoris* via homologous recombination between the transforming DNA and regions of homology within the genome. Such integrants show extreme stability in the absence of selective pressure even when present as multiple copies.

The expression vectors included int his kit carry the HIS4 gene for selection and are designed to be linearized with a restriction enzyme such that HIS+ recombinants can be generated by integration at the his4 locus (a non-deletion, very low spontaneous reversion mutation) or at the AOX1 locus. Integration events at the AOX1 locus can result in the complete removal of the AOX1 coding region (i.e. gene replacement) that in turn results in a recombinant phenotype of His+ Mut− (Mut− refers to the methanol utilization minus phenotype caused by the loss of alcohol oxidase activity encoded by the AOX1 gene that results in a no growth or slow growth phenotype on methanol media). His+ transformants can be readily and easily screened for the Mut− phenotype, indicating integration at the AOX1 locus. The His+ Mut− clones can be further screened for expression of the heterologous protein of interest.

A number of independently isolated His+ Mut− recombinants are routinely screened for expression of the heterologous protein of interest because of the observation of clonal variation (or difference in levels of expressing heterologous protein seen among different transformants with the same phenotype (His+ Mut−)). In some cases this clonal variation can be explained by a difference in the number of copies of the integrated plasmid (i.e. more copies=more expressed protein), but it is not simply copy number that determines protein expression level. There are several examples where one or more copies of the integrants express at the same level (and that level is high), as well as examples where an increase in the integrant copy number causes a decrease in the protein expression level. the best method at this time is to identify a successfully expressing clone among several (10–20) His+ Mut− transformants empirically.

Some examples of heterologous protein expression include:

| Protein | Expression (g/L) | Where Expressed | Reference |
| --- | --- | --- | --- |
| Human serum albumin (HSA) | 4.0 | S | Barr, et al (1992) |
| β-galactosidase | 20,000 (U/mg total protein) | I | Tschopp, et al (1987a) |
| Hepatitis B surface antigen (HBSAg) | 0.4 | I | Cregg, et al (1987) |
| Tumor Necrosis Factor (TNF) | 10.0 | I | Sreekrishna, et al (1988) |
| Invertase | 2.3 | S | Tschopp, et al (1987b) |
| Bovine Iysozyme c2 | 0.55 | S | Digan, et al (1989) |
| Tetanus toxin fragment C | 12.0 | I | Clare, et al (1991a) |
| Pertusis antigen P69 | 3.0 | I | Romanus, et al (1991) |
| Streptokinase (active) | 0.08 | I | Hagenson, et al (1989) |
| Human EGF | 0.5 | S | Cregg, et al (1993) |
| Mouse EGF | 0.45 | S | Claire, et al (1991b) |
| Aprotinin | 0.8 | S | Vedvick, et al (1991) |
| Kunitz protease inhibitor | 1.0 | S | Wagner, et al (1992) |

(S = secreted; I = intracellular)

REFERENCES CITED

1. Anderson, R. A. and Sando, G. N. "Cloning and Expression of cDNA Encoding Human Lysosomal Acid Lipase/Cholesteryl Ester Hydrolase. Similarities to Gastric and Lingual Lipases." J. Biol. Chem. 266:22740–84 (1991);
2. Bernback, Stefan et al. "Purification and Molecular Characterization of Bovine Pregastric Lipase" Eur. J. Biochem. 148:233–238 (1985);
3. Benicourt, Clause et al. "Acides Nucleiques Codant Pour la Lipase Gastrique de Lapin et Derives Polypeptidiques, Leur Utilisation Pour La Production de Ces Polypeptides, et Compositions Pharmaceutiques a Base de Ces Derniers" EP 542,629 dated May 19, 1993;
4. Birschbach, Peter "Pregastric Lipases" Bulletin of the IDF 269:36–39;
5. Blanchard, Claire et al. "Recombinant Canine Gastric Lipase and Pharmaceutical Compositions" WO 94/13816 dated Jun. 24, 1994;
6. Brockerhoff, H. "Determination of the Positional Distribution of Fatty Acids in Glycerolipids" General Analytical Methods 315–325;
7. Carriere, F. et al. "Purification and Biochemical Characterization of Dog Gastric Lipase" Eur. J. Biochem. 202:75–83 (1991);
8. Chapter 12 "Hard Italian Cheeses" Cheese and Fermented Milk Foods 213–227;
9. Chapter 2.12, "Flavor Production with Enzymes," Industrial Enzymology, 2d Ed., Godfrey and West Eds. (Stockton Press, 1996);
10. Chaudhari, R. V. and Richardson, G. H. "Lamb Gastric Lipase and Proteases in Cheese Manufacture" Journal of Dairy Science 54:467–71;
11. Crabbe, Thomas et al. "The Secretion of Active Recombinant Human Gastric Lipase by Saccharymoses cerevisiae" Protein Expression and Purification, 7:229–236 (1996);
12. "Current Protocols in Molecular Biology", John Wiley & Sons, Inc, 1998 (ISBN 0-471-50338-X).
13. De Laborde de Monpesat, Thierry et al. "A Fluorimetric Methof for Measuring Lipase Activity Based on Umbelliferyl Ester" Chemical Abstracts 114:278;
14. Doeherty, A. J. P. et al. "Molecular Cloning and Nucleotide Sequence of Rat Lingual Lipase cDNA" Nucleic Acids Res. 13:1891–1903 (1985);
15. D'Souza, Trevor M. and Oriel, Patrick "Purification and Characterization of Lamb Pregastric Lipase" Applied Biochemistry and Biotechnology 36:183–198 (1992);
16. Eastman Kodak Company "Yeast N-Terminal FLAG® Expression System" FLAG Biosystem 1994;
17. Food Chemicals Codex, (National Academy Press, Washington, D.C., 1981) pp. 480, 493;
18. Fox, P. F. and Law, J. "Enzymology of Cheese Ripening" Food Biotechnology 5:239–262 (1991);
19. Ha, J. Kim and Lindsay, R. C. "Influence of $a_w$ on Volatile Free Fatty Acids during Storage of Cheese Bases Lipolyzed by Kid Goat Pregastric Lipase" Int. Dairy Journal 2:179–193 (1992);
20. Ha, J. Kim and Lindsay, R. C. "Release of Volatile Branched-Chain and Other Fatty Acids From Ruminant Milk Fats by Various Lipases" Chemical Abstracts 118:865–66 (1993);
21. Hamosh, Margit "Lingual and Gastric Lipases" Nutrition 6:421–428 (1990);
22. Komaromy, M. C. and Schotz, M. C. "Cloning of Rat Hepatic Lipase cDNA: Evidence For A Lipase Gene Family" PNAS USA 84:1626–630 (1987);
23. Kurihara, Yoshie et al. "Curculin B and DNA encoding Same, and Process for Production Thereof" AU-B-11415/92 dated Sep. 9, 1992;
24. Lowe, P. A. "New Gastric Lipase Protein, esp. of Human Origin for Treating Lipase Deficiencyy, and DNA Sequences Coding for It" WO/86/01532 dated Mar. 13, 1986;
25. Moreau, H. et al. "Purification, Characterization and Kinetic Properties of the Rabbit Gastric Lipase" Biochimica et Biophysica Acta 960:286–293 (1988);
26. Nelson, J. H. et al. "Pregastric Esterase and Other Oral Lipases-A Review" Journal of Dairy Science 60:327–362 (1976);
27. Parry, R. M., Jr. et al. "Rapid and Sensitive Assay for Milk Lipase" Journal of Dairy Science 49:356–360;
28. Invitrogen Corp. "*Pichia* Expression Kit: Protein Expression" Version 3.0, Catalog No. K1710-01;
29. Invitrogen Corp. "pPIC9K A *Pichia* Vector for Multicopy Integration and Secreted Expression" Version A, Catalog No. V175-20;
30. Ramsey, Harold A. "Electrophoretic Separation of Esterases Present in Various Tissues of the Calf" Journal of Dairy Science 1185–86;
31. Ramsey, Harold A. "Photometric Procedure for Determining Esterase Activity" Clinical Chemistry 3:185–194;
32. Ramsey, H. A. and Young, J. W. "Substrate Specificity of Pregastric Esterase from the Calf" Journal of Dairy Science 2304–2306;
33. Richardson, G. H. et al. "Gastric Lipase Characterization and Utilization in Cheese Manufacture" Journal of Dairy Science 54:643–647;
34. Richardson, G. H. and Nelson, J. H. "Assay and Characterization of Pregastric Esterase" Journal of Dairy Science 50:1061–1065;
35. Sambrook, J. et al. "Molecular Cloning: A Laboratory Manual," (Cold Spring Harbor, 1989);
36. Scorer, Carol A. et al. "Rapid Selection Using G418 of High Copy Number Transformants of *Pichia pastoris* for High-level Foreign Gene Expression," Bio/Technology 12:181 (Feb. 12, 1994);

37. Siezen, R. J. and van den Berg, G. "Lipases and Their Action on Milkfat" Bulletin of the IDF 294:4–6;
38. Sweet, B. J. et al. "Purification and Charaterization of Pregastric Esterase from Calf" Archives of Biochemistry and Biophysics 234:144–150 (1984);
39. Talhoun, M. K. and Abdel-Ghaffar, M. "A Modified Colormetric Method for Assay of Lipase Activity" Chemical Abstracts 106:272;
40. Timmermans, M. Y. J. et al. "The cDNA Sequence Encoding Bovine Pregastric Esterase," Gene 147: 259–262 (1994);
41. U.S. Pat. No. 2,531,329 for "Cheese Modifying Enzyme Product" (issued Nov. 21, 1950);
42. U.S. Pat. No. 2,794,743 for "Enzyme-containing Powder and Enzyme-Modified Product Thereof";
43. U.S. Pat. No. 3,081,225 for "Enzyme Treatment for scours in animals";
44. U.S. Pat. No. 3,256,150 for "Method for Treating Malabsorption Syndrome";
45. U.S. Pat. No. 5,320,959 for "Liquid Lipase From Animal Origin and Method of Preparation" (issued Jun. 14, 1994);
46. U.S. Pat. No. 5,521,088 for "Alcohol Acetyltransferase Genes and Use Thereof" (issued May 28, 1996);
47. U.S. Pat. No. 5,529,917 for "Compositions and Methods For Making Lipolytic Enzymes" (issued Jun. 25, 1996);
48. U.S. Pat. No. 5,372,941 for "Liquid Lipase From Animal Origin" (issued Dec. 13, 1994);
49. U.S. Pat. No. 5,691,181 for "DNA Encoding Lipase From Human Gastric Mucosal Tissue" (issued Nov. 25, 1997);
50. U.S. Pat. No. 5,728,412 for "Alcohol Acetyltransferase Genes and Use Thereof" (issued Mar. 17, 1998); and
51. Vorderwulbecke et al. "Comparison of Lipases by Different Assays" Enzyme Microb. Technol. 14:631–39 (1992).

The claimed invention is:

1. A mixture of fatty acids produced by reacting the kid pregastric esterase SEQ ID NO:2 with a dairy product.

2. The mixture of claim 1, wherein the dairy product comprises lipolyzed butter oil, milk, cheeses or whey.

3. A process for producing a mixture of fatty acids comprising reacting a dairy product with the kid pregastric esterase of claim 1.

* * * * *

SEQUENCE LISTING

<160> NUMBER OF SEQ ID NOS: 7

<210> SEQ ID NO 1
<211> LENGTH: 1134
<212> TYPE: DNA
<213> ORGANISM: Kid (Goat)
<220> FEATURE:
<221> NAME/KEY: CDS
<222> LOCATION: (1)..(1134)

<400> SEQUENCE: 1

```
ttc ctt gga aaa att gct aag aac cct gaa gcc agt atg aat gtg agt        48
Phe Leu Gly Lys Ile Ala Lys Asn Pro Glu Ala Ser Met Asn Val Ser
  1               5                  10                  15 cag atg att tcc ttc tgg ggc tac cca agt gag atg cat aaa gtt ata        96
Gln Met Ile Ser Phe Trp Gly Tyr Pro Ser Glu Met His Lys Val Ile
             20                  25                  30 act gca gat ggc tat atc ctt cag gtc tat cgg att cct cat gga aag       144
Thr Ala Asp Gly Tyr Ile Leu Gln Val Tyr Arg Ile Pro His Gly Lys
         35                  40                  45 aat gat gct aat cat tta ggt cag aga cct gtt gtg ttt ctg cag cat       192
Asn Asp Ala Asn His Leu Gly Gln Arg Pro Val Val Phe Leu Gln His
     50                  55                  60 ggt ctt ctt gcc tca gct aca aac tgg att tcc aac ctt ccc aac aac       240
Gly Leu Leu Ala Ser Ala Thr Asn Trp Ile Ser Asn Leu Pro Asn Asn
 65                  70                  75                  80 agc ctg ggc ttc ctc ctg gca gat gct ggt tat gac gtg tgg ctg ggg       288
Ser Leu Gly Phe Leu Leu Ala Asp Ala Gly Tyr Asp Val Trp Leu Gly
                 85                  90                  95 aac agc aga gga aac act tgg gcc cag gaa cat tta tac tat tca cca       336
Asn Ser Arg Gly Asn Thr Trp Ala Gln Glu His Leu Tyr Tyr Ser Pro
            100                 105                 110 gac tcc cct gaa ttc tgg gct ttc agc ttt gat gaa atg gct gaa tat       384
Asp Ser Pro Glu Phe Trp Ala Phe Ser Phe Asp Glu Met Ala Glu Tyr
        115                 120                 125 gac ctt cca tct aca att gat ttc atc tta aag aga aca gga cag aag       432
Asp Leu Pro Ser Thr Ile Asp Phe Ile Leu Lys Arg Thr Gly Gln Lys
    130                 135                 140 aag cta cac tat gtt ggc cat tcc caa ggc acc acc att ggt ttt gtc       480
Lys Leu His Tyr Val Gly His Ser Gln Gly Thr Thr Ile Gly Phe Val
145                 150                 155                 160 gcc ttt tct acc aat ccc aca ctg gct gaa aaa atc gaa gtc ttc cat       528
Ala Phe Ser Thr Asn Pro Thr Leu Ala Glu Lys Ile Glu Val Phe His
```

-continued

```
                        165                 170                 175
gca tta gcc cca gtc gcc aca gtg aag cac acc cag agc ctg ttt aac         576
Ala Leu Ala Pro Val Ala Thr Val Lys His Thr Gln Ser Leu Phe Asn
            180                 185                 190 aaa ctt gca ctt att cct cac ttc ctc ttc aag att ata ttt ggt aac         624
Lys Leu Ala Leu Ile Pro His Phe Leu Phe Lys Ile Ile Phe Gly Asn
        195                 200                 205 aaa atg ttc tac cca cac aat ttt ttt gaa caa ttt ctt ggt gtt gaa         672
Lys Met Phe Tyr Pro His Asn Phe Phe Glu Gln Phe Leu Gly Val Glu
    210                 215                 220 gtg tgc tct cgt gag aca ctg gat gtc ctt tgt aag aat gcc ttg ttt         720
Val Cys Ser Arg Glu Thr Leu Asp Val Leu Cys Lys Asn Ala Leu Phe
225                 230                 235                 240 gcc att act gga gct gac aat aaa aac ttc aac atg agt cgc tta gat         768
Ala Ile Thr Gly Ala Asp Asn Lys Asn Phe Asn Met Ser Arg Leu Asp
                245                 250                 255 gtg tat gta gca cat aat cca gca gga gct tct gtt caa aac atc ctc         816
Val Tyr Val Ala His Asn Pro Ala Gly Ala Ser Val Gln Asn Ile Leu
            260                 265                 270 cac tgg aga cag gct att aag tct ggg aaa ttc caa gct ttt gac tgg         864
His Trp Arg Gln Ala Ile Lys Ser Gly Lys Phe Gln Ala Phe Asp Trp
        275                 280                 285 gga gcc tca gtt gag aac cta atg cat tat aat cag ccc aca cct ccc         912
Gly Ala Ser Val Glu Asn Leu Met His Tyr Asn Gln Pro Thr Pro Pro
    290                 295                 300 atc tac aat tta aca gcc atg aat gtc cca att gca gta tgg agt gct         960
Ile Tyr Asn Leu Thr Ala Met Asn Val Pro Ile Ala Val Trp Ser Ala
305                 310                 315                 320 ggc caa gac ctg ttg gct gac cct cag gat gtt gac ctt ttg ctt tca        1008
Gly Gln Asp Leu Leu Ala Asp Pro Gln Asp Val Asp Leu Leu Leu Ser
                325                 330                 335 aaa ctc tct aat ctc att cac cac aag gaa att cca aat tac aat cat        1056
Lys Leu Ser Asn Leu Ile His His Lys Glu Ile Pro Asn Tyr Asn His
            340                 345                 350 ctg gac ttt atc tgg gca atg gat gca cct caa gaa gtt tac aat gaa        1104
Leu Asp Phe Ile Trp Ala Met Asp Ala Pro Gln Glu Val Tyr Asn Glu
        355                 360                 365 att att tct ttg atg gca aaa gac aaa aag                                 1134
Ile Ile Ser Leu Met Ala Lys Asp Lys Lys
    370                 375

<210> SEQ ID NO 2
<211> LENGTH: 378
<212> TYPE: PRT
<213> ORGANISM: Kid (Goat)

<400> SEQUENCE: 2

Phe Leu Gly Lys Ile Ala Lys Asn Pro Glu Ala Ser Met Asn Val Ser
  1               5                  10                  15

Gln Met Ile Ser Phe Trp Gly Tyr Pro Ser Glu Met His Lys Val Ile
             20                  25                  30

Thr Ala Asp Gly Tyr Ile Leu Gln Val Tyr Arg Ile Pro His Gly Lys
         35                  40                  45

Asn Asp Ala Asn His Leu Gly Gln Arg Pro Val Val Phe Leu Gln His
     50                  55                  60

Gly Leu Leu Ala Ser Ala Thr Asn Trp Ile Ser Asn Leu Pro Asn Asn
 65                  70                  75                  80

Ser Leu Gly Phe Leu Leu Ala Asp Ala Gly Tyr Asp Val Trp Leu Gly
                 85                  90                  95
```

```
Asn Ser Arg Gly Asn Thr Trp Ala Gln Glu His Leu Tyr Tyr Ser Pro
            100                 105                 110
Asp Ser Pro Glu Phe Trp Ala Phe Ser Phe Asp Glu Met Ala Glu Tyr
        115                 120                 125
Asp Leu Pro Ser Thr Ile Asp Phe Ile Leu Lys Arg Thr Gly Gln Lys
        130                 135                 140
Lys Leu His Tyr Val Gly His Ser Gln Gly Thr Thr Ile Gly Phe Val
145                 150                 155                 160
Ala Phe Ser Thr Asn Pro Thr Leu Ala Glu Lys Ile Glu Val Phe His
                165                 170                 175
Ala Leu Ala Pro Val Ala Thr Val Lys His Thr Gln Ser Leu Phe Asn
            180                 185                 190
Lys Leu Ala Leu Ile Pro His Phe Leu Phe Lys Ile Ile Phe Gly Asn
        195                 200                 205
Lys Met Phe Tyr Pro His Asn Phe Phe Glu Gln Phe Leu Gly Val Glu
    210                 215                 220
Val Cys Ser Arg Glu Thr Leu Asp Val Leu Cys Lys Asn Ala Leu Phe
225                 230                 235                 240
Ala Ile Thr Gly Ala Asp Asn Lys Asn Phe Asn Met Ser Arg Leu Asp
                245                 250                 255
Val Tyr Val Ala His Asn Pro Ala Gly Ala Ser Val Gln Asn Ile Leu
            260                 265                 270
His Trp Arg Gln Ala Ile Lys Ser Gly Lys Phe Gln Ala Phe Asp Trp
        275                 280                 285
Gly Ala Ser Val Glu Asn Leu Met His Tyr Asn Gln Pro Thr Pro Pro
    290                 295                 300
Ile Tyr Asn Leu Thr Ala Met Asn Val Pro Ile Ala Val Trp Ser Ala
305                 310                 315                 320
Gly Gln Asp Leu Leu Ala Asp Pro Gln Asp Val Asp Leu Leu Leu Ser
                325                 330                 335
Lys Leu Ser Asn Leu Ile His His Lys Glu Ile Pro Asn Tyr Asn His
            340                 345                 350
Leu Asp Phe Ile Trp Ala Met Asp Ala Pro Gln Glu Val Tyr Asn Glu
        355                 360                 365
Ile Ile Ser Leu Met Ala Lys Asp Lys Lys
    370                 375

<210> SEQ ID NO 3
<211> LENGTH: 1411
<212> TYPE: DNA
<213> ORGANISM: Kid (Goat)

<400> SEQUENCE: 3
gaattcggca cgagttttca tttaccttcg agaaactaga aggcattcac tttggtgaca      60
attgaaaatg tggtggctac ttgtaacggt gtgtttcatc cacatgtctg gaaatgcatt    120
ttgtttcctt ggaaaaattg ctaagaaccc tgaagccagt atgaatgtga gtcagatgat    180
ttccttctgg ggctacccaa gtgagatgca taaagttata actgcagatg gctatatcct    240
tcaggtctat cggattcctc atggaaagaa tgatgctaat catttaggtc agagacctgt    300
tgtgtttctg cagcatggtc ttcttgcctc agctacaaac tggatttcca accttcccaa    360
caacagcctg gcttcctcc tgcagatgc tggttatgac gtgtggctgg ggaacagcag    420
aggaaacact tgggcccagg aacatttata ctattcacca gactcccctg aattctgggc    480
```

-continued

```
tttcagctttt gatgaaatgg ctgaatatga ccttccatct acaattgatt tcatcttaaa        540
gagaacagga cagaagaagc tacactatgt tggccattcc caaggcacca ccattggttt        600
tgtcgccttt tctaccaatc ccacactggc tgaaaaaatc gaagtcttcc atgcattagc        660
cccagtcgcc acagtgaagc acacccagag cctgtttaac aaacttgcac ttattcctca        720
cttcctcttc aagattatat ttggtaacaa aatgttctac ccacacaatt tttttgaaca        780
atttcttggt gttgaagtgt gctctcgtga gacactggat gtcctttgta agaatgcctt        840
gtttgccatt actggagctg acaataaaaa cttcaacatg agtcgcttag atgtgtatgt        900
agcacataat ccagcaggag cttctgttca aacatcctc cactggagac aggctattaa         960
gtctgggaaa ttccaagctt ttgactgggg agcctcagtt gagaacctaa tgcattataa       1020
tcagcccaca cctcccatct acaatttaac agccatgaat gtcccaattg cagtatggag       1080
tgctggccaa gacctgttgg ctgaccctca ggatgttgac cttttgcttt caaaactctc       1140
taatctcatt caccacaagg aaattccaaa ttacaatcat ctggacttta tctgggcaat       1200
ggatgcacct caagaagttt acaatgaaat tatttctttg atggcaaaag acaaaaagta       1260
gttctggatt tagagaatta ttcatttact tttccaaaa tagtttcttc tcacctacat        1320
gatttctgta ctgttataaa cgcaatgctt cttctgtaa tgttgacttt caaaatatat        1380
tagcatcaac aaaaaaactc gtgccgaatt c                                      1411
```

<210> SEQ ID NO 4
<211> LENGTH: 1134
<212> TYPE: DNA
<213> ORGANISM: bovine

<400> SEQUENCE: 4

```
ttccttggaa aaattgctaa gaaccctgaa gccagtatga atgttagtca gatgatttcc         60
tactggggct acccaagtga gatgcataaa gttataactg cggatggtta tatccttcag        120
gtctatcgga ttcctcatgg aaagaataat gctaatcatt taggtcagag acctgttgtg        180
tttctgcagc atggtcttct tggatcagcc acaaactgga tttccaacct gcccaagaac        240
agcctgggct tcctcctggc agatgctggt tatgacgtgt ggctggggaa cagcagagga        300
aacacctggg cccaggaaca tttatactat tcaccagact ccccggaatt ctgggctttc        360
agctttgatg aaatggcgga atatgacctt ccatctacaa ttgatttcat cttaaggaga        420
acaggacaga agaagctaca ctatgttggc cattcccaag caccaccat ggttttatc         480 gccttttcta ccagtcccac attggctgaa aaatcaaag tcttctatgc attagcccca        540
gttgccacag tgaagtacac caagagcctg tttaacaaac ttgcacttat tcctcacttc        600
ctcttcaaga ttatatttgg tgacaaaatg ttctacccac acactttttt ggaacaattt        660
cttggtgttg aaatgtgctc ccgtgagaca ctggatgtcc tttgtaagaa tgccttgttt        720
gccattactg gagttgacaa taaaaacttc aacatgagtc gcttagatgt gtatatagca        780
cataatccag caggaacttc tgttcaaaac ccctccact ggagacaggc tgttaagtct         840
gggaaattcc aagcttttga ctggggagcc ccatatcaga acctaatgca ttatcatcag        900
cccacacctc ccatctacaa tttaacagcc atgaatgtcc caattgcagt atggagtgct        960
gacaatgacc tgttggctga ccctcaggat gttgactttc tgctttcaaa actctctaat       1020
ctcatttacc acaaggaaat tccaaattac aatcacttgg actttatctg ggcaatggat       1080
gcacctcaag aagtttacaa tgaaattgtt ctttgatgg ccgaagacaa aaag              1134
```

<210> SEQ ID NO 5
<211> LENGTH: 8324
<212> TYPE: DNA
<213> ORGANISM: Yeast YE-1 expression vector

<400> SEQUENCE: 5

| | | | | | |
|---|---|---|---|---|---|
| gatccttcaa | tatgcgcaca | tacgctgtta | tgttcaaggt | cccttcgttt | aagaacgaaa | 60 |
| gcggtcttcc | ttttgaggga | tgtttcaagt | tgttcaaatc | tatcaaattt | gcaaatcccc | 120 |
| agtctgtatc | tagagcgttg | aatcggtgat | gcgatttgtt | aattaaattg | atggtgtcac | 180 |
| cattaccagg | tctagatata | ccaatggcaa | actgagcaca | acaataccag | tccggatcaa | 240 |
| ctggcaccat | ctctcccgta | gtctcatcta | attttttctc | cggatgaggt | tccagatata | 300 |
| ccgcaacacc | tttattatgg | tttccctgag | ggaataatag | aatgtcccat | tcgaaatcac | 360 |
| caattctaaa | cctgggcgaa | ttgtatttcg | ggtttgttaa | ctcgttccag | tcaggaatgt | 420 |
| tccacgtgaa | gctatcttcc | agcaaagtct | ccacttcttc | atcaaattgt | ggagaatact | 480 |
| cccaatgctc | ttatctatgg | gacttccggg | aaacacagta | ccgatacttc | ccaattcgtc | 540 |
| ttcagagctc | attgtttgtt | tgaagagact | aatcaaagaa | tcgttttctc | aaaaaaatta | 600 |
| atatcttaac | tgatagtttg | atcaaagggg | caaaacgtag | gggcaaacaa | acggaaaaat | 660 |
| cgtttctcaa | attttctgat | gccaagaact | ctaaccagtc | ttatctaaaa | attgccttat | 720 |
| gatccgtctc | tccggttaca | gcctgtgtaa | ctgattaatc | ctgcctttct | aatcaccatt | 780 |
| ctaatgtttt | aattaaggga | ttttgtcttc | attaacggct | ttcgctcata | aaaatgttat | 840 |
| gacgttttgc | ccgcaggcgg | gaaaccatcc | acttcacgag | actgatctcc | tctgccggaa | 900 |
| caccgggcat | ctccaactta | taagttggag | aaataagaga | atttcagatt | gagagaatga | 960 |
| aaaaaaaaa | aaaaaaaag | gcagaggaga | gcatagaaat | ggggttcact | ttttggtaaa | 1020 |
| gctatagcat | gcctatcaca | tataaataga | gtgccagtag | cgactttttt | cacactcgaa | 1080 |
| atactcttac | tactgctctc | ttgttgtttt | tatcacttct | tgtttcttct | tggtaaatag | 1140 |
| aatatcaagc | tacaaaaagc | atacaatcaa | ctatcaacta | ttaactatat | cgtaatacac | 1200 |
| caagctcgac | ctcgcgatga | gatttccttc | aatttttact | gcagttttat | tcgcagcatc | 1260 |
| ctccgcatta | gctgctccag | tcaacactac | aacagaagat | gaaacggcac | aaattccggc | 1320 |
| tgaagctgtc | atcggttact | agatttaga | aggggatttc | gatgttgctg | ttttgccatt | 1380 |
| ttccaacagc | acaaataacg | ggttattgtt | tataaatact | actattgcca | gcattgctgc | 1440 |
| taaagaagaa | ggggtacctt | tggataaaag | acaccaccac | caccaccacc | accaccacca | 1500 |
| ctcttctggt | cacatcgacg | acgacgacaa | gttcttgggt | aaaattgcta | agaaccctga | 1560 |
| agccagtatg | aatgtgagtc | agatgatttc | cttctgggc | tacccaagtg | agatgcataa | 1620 |
| agttataact | gcagatggct | atatccttca | ggtctatcgg | attcctcatg | gaaagaatga | 1680 |
| tgctaatcat | ttaggtcaga | gacctgttgt | gtttctgcag | catggtcttc | ttgcctcagc | 1740 |
| tacaaactgg | atttccaacc | ttcccaacaa | cagcctgggc | ttcctcctgg | cagatgctgg | 1800 |
| ttatgacgtg | tggctgggga | acagcagagg | aaacacttgg | gcccaggaac | atttatacta | 1860 |
| ttcaccagac | tcccctgaat | tctgggcttt | cagctttgat | gaaatggctg | aatatgacct | 1920 |
| tccatctaca | attgatttca | tcttaaagag | aacaggacag | aagaagctac | actatgttgg | 1980 |
| ccattcccaa | ggcaccacca | ttggttttgt | cgccttttct | accaatccca | cactggctga | 2040 |
| aaaaatcgaa | gtcttccatg | cattagcccc | agtcgccaca | gtgaagcaca | cccagagcct | 2100 |
| gtttaacaaa | cttgcactta | ttcctcactt | cctcttcaag | attatatttg | gtaacaaaat | 2160 |

-continued

```
gttctaccca cacaattttt ttgaacaatt tcttggtgtt gaagtgtgct ctcgtgagac    2220
actggatgtc ctttgtaaga atgccttgtt tgccattact ggagctgaca ataaaaactt    2280
caacatgagt cgcttagatg tgtatgtagc ataatccaa gcaggagctt ctgttcaaaa    2340
catcctccac tggagacagg ctattaagtc tgggaaattc aagcttttg actggggagc    2400 ctcagttgag aacctaatgc attataatca gcccacacct cccatctaca atttaacagc    2460
catgaatgtc ccaattgcag tatggagtgc tggccaagac ctgttggctg accctcagga    2520
tgttgaccct ttgctttcaa aactctctaa tctcattcac cacaaggaaa ttccaaatta    2580
caatcatctg gactttatct gggcaatgga tgcacctcaa gaagtttaca atgaaattat    2640
ttctttgatg gcaaaagaca aaagtagta agcggccgct gatccgtcga gcgtcccaaa    2700
accttctcaa gcaaggtttt cagtataatg ttacatgcgt acacgcgtct gtacagaaaa    2760 aaagaaaaa tttgaaatat aaataacgtt cttaatacta acataactat aaaaaaataa    2820
atagggacct agacttcagg ttgtctaact ccttcctttt cggttagagc ggatgtgggg    2880
ggagggcgtg aatgtaagcg tgacataact aattacatga tatcgacctg cagccaagct    2940
ttgaagaaaa atgcgcctta ttcaatcttt gctataaaaa atggcccaaa atctcacatt    3000
ggaagacatt tgatgacctc atttctttca atgaagggcc taacggagtt gactaatgtt    3060
gtgggaaatt ggagcgataa gcgtgcttct gccgtggcca ggacaacgta tactcatcag    3120
ataacagcaa tacctgatca ctacttcgca ctagtttctc ggtactatgc atatgatcca    3180
atatcaaagg aaatgatagc attgaaggat gagactaatc caattgagga gtggcagcat    3240
atagaacagc taaagggtag tgctgaagga agcatacgat accccgcatg gaatgggata    3300
atatcacagg aggtactaga ctaccttta tcctacataa atagacgcat ataagtacgc    3360
atttaagcat aaacacgcac tatgccgttc ttctcatgta tatatatata caggcaacac    3420
gcagatatag gtgcgacgtg aacagtgagc tgtatgtgcg cagctcgcgt tgcattttcg    3480
gaagcgctcg ttttcggaaa cgctttgaag ttcctattcc gaagttccta ttctctagaa    3540
agtataggaa cttcagagcg cttttgaaaa ccaaaagcgc tctgaagacg cactttcaaa    3600
aaaccaaaaa cgcaccggac tgtaacgagc tactaaaata ttgcgaatac cgcttccaca    3660
aacattgctc aaaagtatct ctttgctata tatctctgtg ctatatccct atataaccta    3720
cccatccacc tttcgctcct tgaacttgca tctaaactcg acctctacat tttttatgtt    3780
tatctctagt attactcttt agacaaaaaa attgtagtaa gaactattca tagagtgaat    3840
cgaaaacaat acgaaaatgt aaacatttcc tatacgtagt atatagagac aaaatagaag    3900
aaaccgttca taattttctg accaatgaag aatcatcaac gctatacctt tctgttcaca    3960
aagtatgcgc aatccacatc ggtatagaat ataatcgggg atgcctttat cttgaaaaaa    4020
tgcacccgca gcttcgctag taatcagtaa acgcgggaag tggagtcagg cttttttttat    4080 ggaagagaaa atagacacca agtagccctt cttctaacct taacgaccct acagtgcaaa    4140
aagttatcaa gagactgcat tatagagcgc acaaggaga aaaaagtaa tctaagatgc    4200 tttgttagaa aaatagcgct ctcgggatgc attttgtag aacaaaaag aagtatagat    4260 tctttgttgg taaatagcg ctctcgcgtt gcatttctgt tctgtaaaaa tgcagctcag    4320
attctttgtt tgaaaatta gcgctctcgc gttgcatttt tgttttacaa aaatgaagca    4380
cagattcttc gttggtaaaa tagcgctttc gcgttgcatt tctgttctgt aaaaatgcag    4440
ctcagattct tgtttgaaa aattagcgct ctcgcgttgc attttgttc tacaaaatga    4500 agcacagatg cttcgttaac aaagatatgc tattgaagtg caagatggaa acgcagaaaa    4560
```

-continued

```
tgaaccgggg atgcgacgtg caagattacc tatgcaatag atgcaatagt ttctccagga    4620
accgaaatac atacattgtc ttccgtaaag cgctagacta tatattatta tacaggttca    4680
aatatactat ctgtttcagg gaaaactccc aggttcggat gttcaaaatt caatgatggg    4740
taacaagtac gatcgtaaat ctgtaaaaca gtttgtcgga tattaggctg tatctcctca    4800
aagcgtattc gaatatcatt gagaagctgc tgcaggcaag tgcacaaaca atacttaaat    4860
aaatactact cagtaataac ctatttctta gcatttttga cgaaatttgc tattttgtta    4920
gagtcttttta caccatttgt ctccacacct ccgcttacat caacaccaat aacgccattt    4980
aatctaagcg catcaccaac attttctggc gtcagtccac cagctaacat aaaatgtaag    5040
ctttcggggc tctcttgcct tccaacccag tcagaaatcg agttccaatc caaaagttca    5100
cctgtcccac ctgcttctga atcaaacaag ggaataaacg aatgaggttt ctgtgaagct    5160
gcactgagta gtatgttgca gtctttttgga aatacgagtc ttttaataac tggcaaaccg    5220
aggaactctt ggtattcttg ccacgactca tctccatgca gttggacgat atcaatgccg    5280
taatcattga ccagagccaa acatcctcc ttaggttgat tacgaaacac gccaaccaag    5340
tatttcggag tgcctgaact atttttatat gcttttacaa gacttgaaat tttccttgca    5400
ataaccgggt caattgttct ctttctattg ggcacacata taatacccag caagtcagca    5460
tcggaatcta gagcacattc tgcggcctct gtgctctgca agccgcaaac tttcaccaat    5520
ggaccagaac tacctgtgaa attaataaca gacatactcc aagctgcctt tgtgtgctta    5580
atcacgtata ctcacgtgct caatagtcac caatgccctc cctcttggcc ctctcctttt    5640
ctttttttcga ccgaattaat tcttgaagac gaaagggcct cgtgatacgc ctatttttat    5700
aggttaatgt catgataata atggtttctt agacgtcagg tggcacttttt cggggaaatg    5760
tgcgcggaac ccctatttgt ttattttttct aaatacattc aaatatgtat ccgctcatga    5820
gacaataacc ctgataaatg cttcaataat attgaaaaag gaagagtatg agtattcaac    5880
atttccgtgt cgcccttatt cccttttttg cggcattttg ccttcctgtt tttgctcacc    5940
cagaaacgct ggtgaaagta aaagatgctg aagatcagtt gggtgcacga gtgggttaca    6000
tcgaactgga tctcaacagc ggtaagatcc ttgagagttt tcgccccgaa gaacgttttc    6060
caatgatgag cacttttaaa gttctgctat gtggcgcggt attatcccgt gttgacgccg    6120
ggcaagagca actcggtcgc cgcatacact attctcagaa tgacttggtt gagtactcac    6180
cagtcacaga aaagcatctt acggatggca tgacagtaag agaattatgc agtgctgcca    6240
taaccatgag tgataacact gcggccaact tacttctgac aacgatcgga ggaccgaagg    6300
agctaaccgc ttttttgcac aacatggggg atcatgtaac tcgccttgat cgttgggaac    6360
cggagctgaa tgaagccata ccaaacgacg agcgtgacac cacgatgcct gcagcaatgg    6420
caacaacgtt gcgcaaacta ttaactggcg aactacttac tctagcttcc cggcaacaat    6480
taatagactg gatggaggcg gataaagttg caggaccact tctgcgctcg gcccttccgg    6540
ctggctggtt tattgctgat aaatctggag ccggtgagcg tgggtctcgc ggtatcattg    6600
cagcactggg gccagatggt aagccctccc gtatcgtagt tatctacacg acgggagtc    6660
aggcaactat ggatgaacga atagacaga tcgctgagat aggtgcctca ctgattaagc    6720
attggtaact gtcagaccaa gtttactcat atatacttta gattgattta aaacttcatt    6780
tttaattaa aaggatctag gtgaagatcc ttttttgataa tctcatgacc aaaatccctt    6840
aacgtgagtt ttcgttccac tgagcgtcag accccgtaga aaagatcaaa ggatcttctt    6900
```

```
gagatccttt ttttctgcgc gtaatctgct gcttgcaaac aaaaaaacca ccgctaccag    6960
cggtggtttg tttgccggat caagagctac caactctttt tccgaaggta actggcttca    7020
gcagagcgca gataccaaat actgtccttc tagtgtagcc gtagttaggc caccacttca    7080
agaactctgt agcaccgcct acatacctcg ctctgctaat cctgttacca gtggctgctg    7140
ccagtggcga taagtcgtgt cttaccgggt tggactcaag acgatagtta ccggataagg    7200
cgcagcggtc gggctgaacg gggggttcgt gcacacagcc cagcttggag cgaacgacct    7260
acaccgaact gagataccta cagcgtgagc tatgagaaag cgccacgctt cccgaaggga    7320
gaaaggcgga caggtatccg gtaagcggca gggtcggaac aggagagcgc acgagggagc    7380
ttccaggggg aaacgcctgg tatctttata gtcctgtcgg gtttcgccac ctctgacttg    7440
agcgtcgatt tttgtgatgc tcgtcagggg gcggagcct atggaaaaac gccagcaacg    7500
cggccttttt acggttcctg gccttttgct ggccttttgc tcacatgttc tttcctgcgt    7560
tatcccctga ttctgtggat aaccgtatta ccgcctttga gtgagctgat accgctcgcc    7620
gcagccgaac gaccgagcgc agcgagtcag tgagcgagga agcggaagag cgcctgatgc    7680
ggtattttct ccttacgcat ctgtgcggta tttcacaccg catatggtgc actctcagta    7740
caatctgctc tgatgccgca tagttaagcc agtatacact ccgctatcgc tacgtgactg    7800
cagatcctga cgcgccctgt agcggcgcat aagcgcggc gggtgtggtg gttacgcgca    7860
gcgtgaccgc tacacttgcc agcgccctag cgcccgctcc tttcgctttc ttcccttcct    7920
ttctcgccac gttcgccggc tttccccgtc aagctctaaa tcgggcatc cctttagggt    7980 tccgatttag tgctttacgg cacctcgacc ccaaaaaact tgattagggt gatggttcac    8040
gtagtgggcc atcgccctga tagacggttt ttcgcccttt gacgttggag tccacgttct    8100
ttaatagtgg actcttgttc caaactggaa caacactcaa ccctatctcg gtctattctt    8160
ttgatttata agggattttg ccgatttcgg cctattggtt aaaaaatgag ctgatttaac    8220
aaaaatttaa cgcgaatttt aacaaaatat taacaaaata ttaacgttta caggatctga    8280
attaattcta ttgagaagat ttaaaggtat ttgacagtag atca    8324
```

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: A modified
      polyHis-enterokinase polypeptide sequence

<400> SEQUENCE: 6

His His His His His His His His His His Ser Ser Gly His Ile Asp
 1               5                  10                  15

Asp Asp Asp Lys
         20

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence: A modified
      polyHis-enterokinase coding nucleic acid sequence

<400> SEQUENCE: 7
caccaccacc accaccacca ccaccaccac tcttctggtc acatcgacga cgacgacaag    60